(12) United States Patent
Flaishman et al.

(10) Patent No.: US 8,148,603 B2
(45) Date of Patent: Apr. 3, 2012

(54) **TRANSGENIC *FICUS*, METHOD FOR PRODUCING SAME AND USE THEREOF**

(75) Inventors: Moshe Flaishman, Tel-Aviv (IL); Avi Pearl, Rishon-LeZion (IL); Sara Golobowicz, Holon (IL)

(73) Assignee: The State of Israel, Ministry of Agriculture & Rural Development, Agricultural Research Organization, (A.R.O.), Volcani Center, Beit-Dagan (IL)

( * ) Notice: Subject to any disclaimer, the term of this patent is extended or adjusted under 35 U.S.C. 154(b) by 335 days.

(21) Appl. No.: 11/597,661

(22) PCT Filed: May 24, 2005

(86) PCT No.: PCT/IL2005/000532
§ 371 (c)(1),
(2), (4) Date: Nov. 24, 2006

(87) PCT Pub. No.: WO2005/115130
PCT Pub. Date: Dec. 8, 2005

(65) Prior Publication Data
US 2007/0248596 A1 Oct. 25, 2007

Related U.S. Application Data

(60) Provisional application No. 60/573,375, filed on May 24, 2004.

(51) Int. Cl.
*A01H 1/00* (2006.01)
*C07H 21/04* (2006.01)
*C12N 15/00* (2006.01)

(52) U.S. Cl. ......... 800/278; 435/6.1; 435/468; 435/419; 435/320.1; 530/370; 536/23.1; 536/24.1; 536/25.1; 800/295

(58) Field of Classification Search .............. 435/6, 468, 435/419, 320.1, 6.1; 530/370; 536/23.1, 536/24.1, 25.1; 800/278, 295
See application file for complete search history.

(56) References Cited

U.S. PATENT DOCUMENTS

| 4,956,282 | A | | 9/1990 | Goodman et al. | |
|---|---|---|---|---|---|
| 5,262,316 | A | * | 11/1993 | Engler et al. | 800/294 |
| 5,608,147 | A | * | 3/1997 | Kaphammer | 800/294 |
| 5,942,660 | A | * | 8/1999 | Gruys et al. | 800/298 |
| 6,235,860 | B1 | * | 5/2001 | Kang et al. | 528/1 |
| 6,261,561 | B1 | * | 7/2001 | Stewart et al. | 424/184.1 |
| 6,444,470 | B1 | * | 9/2002 | Ross et al. | 435/468 |
| 6,455,315 | B1 | | 9/2002 | Baszczynski et al. | |
| 6,858,777 | B2 | * | 2/2005 | Zhong et al. | 800/294 |
| 7,186,887 | B2 | * | 3/2007 | Kreps et al. | 800/286 |

OTHER PUBLICATIONS

International Preliminary Report on Patentability Dated Dec. 7, 2006 From the International Bureau of WIPO Re.: Application No. PCT/IL05/00532.
International Search Report Dated May 4, 2006 From the International Searching Authority Re.: Application No. PCT/IL05/00532.
Written Opinion Dated May 4, 2006 From the International Searching Authority Re.: Application No. PCT/IL05/00532.

* cited by examiner

*Primary Examiner* — Phuong Bui

(57) ABSTRACT

The present invention relates to transgenic *Ficus* plants, particularly *Ficus carica* (fig tree), to a method for producing same, and to *Ficus* plants, plant materials and plant products produced by or from such genetically modified plant material. More specifically, the present invention relates to transgenic *Ficus carica* plants and use thereof for producing trees having improved agricultural traits and for the production of foreign proteins and edible vaccines.

26 Claims, 9 Drawing Sheets

Brown Turkey

Smyrna

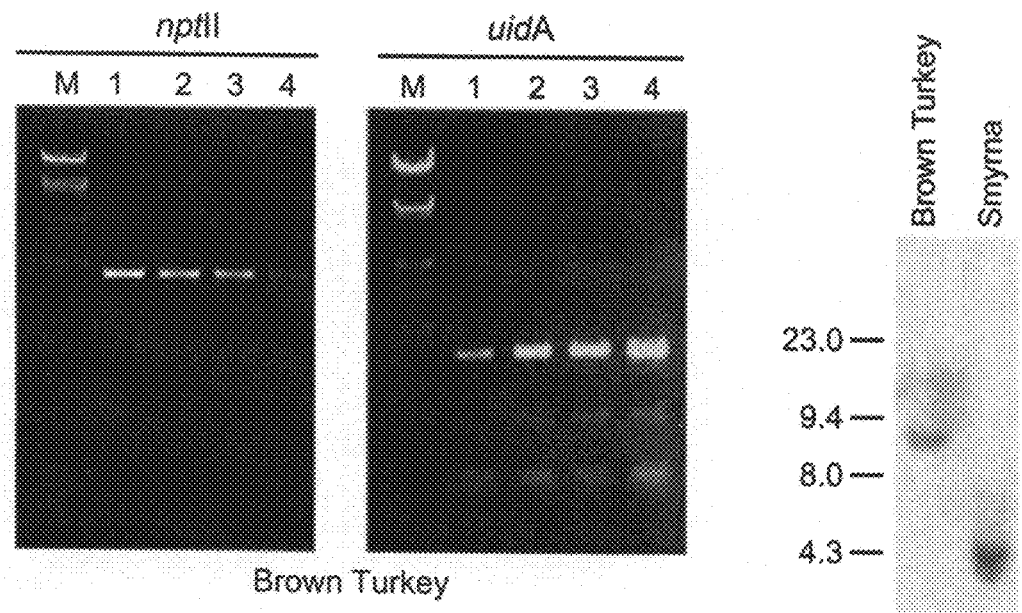
Fig. 8a
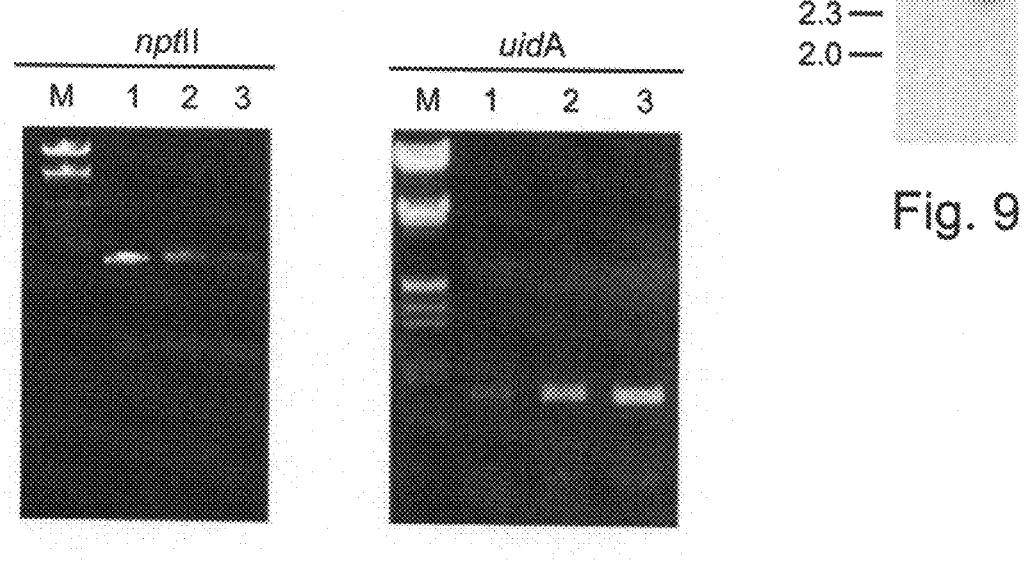
Fig. 8b
Fig. 9

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
gccgcttggg tggagaggct at                                           22

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
gaggaagcgg tcagcccatt c                                            21

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide
```

```
<400> SEQUENCE: 3
cgagcgattt ggtcatgtga ag                                              22

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4
cattgtttgc ctccctgctg cggtt                                           25
```

TRANSGENIC *FICUS*, METHOD FOR PRODUCING SAME AND USE THEREOF

RELATED APPLICATIONS

This Application is a National Phase of PCT Patent Application No. PCT/IL2005/000532 having International Filing Date of May 24, 2005, which claims the benefit of U.S. Provisional Patent Application No. 60/573,375 filed on May 24, 2004. The contents of the above Applications are all incorporated herein by reference.

FIELD OF THE INVENTION

The present invention relates to genetically modified *Ficus* plants, particularly *Ficus carica* (fig tree), to a method for producing same, and to *Ficus* plants, plant materials and plant products produced by or from such genetically modified plant material. More specifically, the present invention relates to a method for efficient transformation and regeneration of *Ficus carica* plants and use thereof for producing trees having improved agricultural traits and for the production of foreign proteins and edible vaccines.

BACKGROUND OF THE INVENTION

The genus *Ficus* of the Moraceae family is a large genus including about 30 species. *Ficus* species are commonly used in gardening, in private as well as in public gardens. Most species bear fruit; however, in several species, fruit is considered a problem since the fruit are in-edible and falling fruit litter sidewalks and other pathways. The edible fruit, on the other hand, are highly desired as they are tasty and nutritional.

Fig trees are one of the earliest fruit bearing trees cultivated. *Ficus carica* L. (Moraceae), the well-known fig of commerce is indigenous to areas from Asiatic Turkey to North India, and natural varieties are cultivated in most of the Mediterranean countries. The fig is well known for its nutritive value, and is consumed fresh or as dried fruit worldwide. The fig fruits are also known for their mild laxative activity and high alkalinity, and substances derived therefrom are used in various drug preparations. Other parts of fig trees have also been shown to have a commercial value.

For example, U.S. Pat. No. 6,235,860 has recently disclosed the use of *Ficus carica* as a source for natural rubber.

U.S. Pat. No. 5,494,669 relates to a skin disorder known as pseudofolliculitis barbae (PFB), and more particularly to a preparation for treating PFB. The preparation disclosed is a topical solution comprising a mixture of alophatic alcohol, liquid aloe, liquid camphor, and the soluble materials of the fresh fig leaves of *Ficus Carica*. Similar compositions are disclosed as a massage composition (U.S. Pat. No. 4,582,706).

U.S. Pat. No. 6,184,193 discloses a shrinkage prevention agent for wet washing of clothing that would conventionally have been dry-cleaned. The shrinkage prevention agent disclosed comprises a steam or vacuum dry-distilled liquid of bark, leaves, stems or flowers of two or more plants, including *Ficus carica*.

Traditional breeding methods of *Ficus carica* require a long-term effort for improving traits of fig trees. Among the *Ficus carica* some trees bear only female synconium and others, named caprifig, bear both male and female flowers. True fruits can be produced only on tress bearing female synconium and cross-pollination is mediated by a specific wasp. Thus, traits donated by the stamens are hard to track.

The application of genetic engineering techniques to stably incorporate homologous and/or heterologous genetic material into woody species, including fruit trees, offers the potential of obtaining improved planting stocks for private and public gardens and for agricultural use in a short period of time compared to those developed using traditional breeding techniques. In addition, efficient transformation methods can be used for the production of heterologous polypeptides having nutritional and/or pharmaceutical value, including edible vaccines.

Plants have the capacity to express foreign genes from a wide range of sources, including viral, bacterial, fungal, insect, animal, and other plant species. In single-copy nuclear transgenics, foreign protein in excess of 1% of total protein is often achieved (Hiatt et al., 1989. Nature 342:76-78). Further, assembly and processing of complex animal proteins in plants is possible, e.g., human serum albumin (Sijmons et al., 1990. Bio/Technology 8:217-220) and secretory antibodies (Ma et al., 1995. Science 268:716-719.). Expression of correctly processed avidin in corn seed at a level of 2% of the total soluble protein was also reported (Hood et al., 1997. Mol. Breeding. 3:291-306). It has been estimated that the cost of recombinant protein production in plants (assuming the foreign protein is 10% of total protein) can be 10 to 50 times less than in *E. coli* by fermentation (Kusnadi et al., 1997. Biotechnol. Bioeng. 56:473-484). Many plant species are now amenable to gene transfer, and numerous number of patents disclose different plant species capable of expressing foreign proteins; U.S. Pat. No. 6,392,121 discloses a system for gene amplification based on plant viral genetic elements that can be used to increase the production of foreign proteins within the plant.

Vaccines are administered to humans and animals to induce their immune systems to produce antibodies against viruses, bacteria, and other types of pathogenic organisms. In the economically advanced countries of the world, vaccines have brought many diseases under control. In particular, many viral diseases are now prevented due to the development of immunization programs. However, many vaccines for various diseases including poliomyelitis, measles, mumps, rabies, foot and mouth, and hepatitis B are still too expensive for the lesser-developed countries to provide to their large human and animal populations. Because of simplicity of delivery of vaccines by oral delivery, there is great current interest in discovering new oral vaccine technologies. Appropriately delivered oral immunogens can stimulate both humoral and cellular immunity and have the potential to provide cost-effective, safe vaccines for use in developing countries or inner cities where large-scale parenteral immunization is not practical or extremely difficult to implement. Such vaccines may be based upon bacterial or viral vector systems expressing protective epitopes from diverse pathogens (multivalent vaccines) or may be based upon purified antigens delivered singularly or in combination with relevant antigens or other pathogens. Several methods for using transgenic plants for oral immunization have been disclosed, for example International Patent Application WO 99/54452; U.S. Pat. Nos. 5,484,719; 5,612,487: 5,914,123; 6,034,320; 6,084, 152; 6,194,123; 6,395,964 and 6,444,805.

The overall efficiency of techniques for genetically modifying plants depends upon the efficiency of the transformation technique(s) used to stably incorporate the required genetic material into plant cells or tissues, and the regeneration technique(s) used to produce viable plants from transformed cells.

Within *Ficus* species, there were some reports on regeneration and organogenesis from callus and explants. *Ficus*

*religiosa* plants have been regenerated from callus of stem segments (Jaiswal and Narayan, 1985. Plant Cell Reports 4:256-258) and leaf callus (Narayan and Jaiswal, 1986. Ind. J. Exper. Biol.24:193-194). Regeneration of *Ficus lyrata* plants from the axillary buds of a mature tree, and the formation of buds from leaf explants were also reported (Deshpande et al., 1998. Plant Cell Reports 17:571-573). However, for in vitro work with figs, plant regeneration has been restricted to the use of single shoot tips and apical buds.

Recently, Yakushiji et al. (J. of Hort. Sci. & Biotech. 2003, 78, 874-878) reported a method for the induction of organogenesis from leaf explants of *Ficus carica* using phloroglucinol (PG). However, by this method the frequency obtained for adventitious bud differentiation from leaf fragments was relatively low, and no adventitious buds were observed without PG. Moreover, regeneration was obtained only with non-transformed leaf segments. Although methods for transformation of woody plants have been reported (for example U.S. Pat. No. 6,255,559), no method for the introduction of isolated genetic material into *Ficus* species was hitherto disclosed.

Thus, there is a recognized need for, and it would be highly advantageous to have efficient methods for both transformation and regeneration of commercially valuable *Ficus* species, specifically fig trees, providing de novo origination of plant material from transformed cells and development of the genetically modified plant material to produce genetically modified plants.

SUMMARY OF THE INVENTION

The present invention relates to transgenic *Ficus* species, particularly to the commercially valuable fig tree *Ficus carica*, comprising exogenous polynucleotides homologous or heterologous to the target *Ficus* genome and to transgenic *Ficus* species capable of expressing exogenous polynucleotides. The present invention further relates to methods for efficient transformation and regeneration of *Ficus* species. The present invention also relates to genetically modified *Ficus* species having improved agronomical traits, useful, inter alia, for production of foreign proteins and production of edible vaccines.

According to one aspect, the present invention provides transgenic *Ficus* species, specifically *Ficus carica*, comprising a genetic construct comprising at least one exogenous polynucleotide.

According to one embodiment, the genetic construct further comprises one or more regulatory elements to confer functional expression of the exogenous polynucleotide in the target *Ficus* plant. As used herein, the term "regulatory element" refers to a non-coding polynucleotide regulating the expression of the exogenous polynucleotide. Regulatory elements include, for example, constitutive, inducible or tissue-specific promoters; enhancer elements; termination elements; transposable elements; and post-transcriptional regulatory elements. The practice of the present invention is not bound to a specific construct and any construct suitable for plant transformation as is known to a person skilled in the art can be used. Introduction of the genetic material into the *Ficus* plant can be performed by any suitable transformation method, including, but not limited to, *Agrobacterium*-mediated introduction, protoplast fusion, viral-mediated transformation, high velocity projectile introduction, electroporation, injection into reproductive organs, and injection into immature embryos.

According to yet another embodiment, the genetic construct according to the present invention further comprises a selection marker. Selection markers are well known in the art, and the selection technique may vary depending upon the selection marker used. According to one embodiment, the selection marker is a gene inducing antibiotic resistance, enabling the survival of the transgenic *Ficus* plants in a medium containing the antibiotic as a selection agent. According to another embodiment, the selection marker is a reporter gene. The reporter gene can encode a fluorescent protein, a chemiluminescent protein, a protein having a detectable enzymatic activity and the like, as is known to a person skilled in the art.

According to yet another embodiment, the selection marker is a herbicide resistance gene, enabling the survival of the transgenic *Ficus* plants in a medium containing the herbicide as a selection agent.

According to further embodiment the exogenous polynucleotide is an exogenous polynucleotide selected from the group consisting of polynucleotides homologous to the *Ficus* genome and polynucleotides heterologous to the *Ficus* genome. The polynucleotide may be selected from a polynucleotide encoding a polypeptide or a functional portion of a polypeptide, a polynucleotide encoding a regulatory factor, such as a transcription factor, a non-coding polynucleotide such as a regulatory polynucleotide, and antisense polynucleotide that inhibit expression of a specified polypeptide.

According to one embodiment, the transgenic *Ficus* plant comprises a polynucleotide conferring a desirable agronomical trait selected from the group consisting of, but not limited to, insect tolerance, disease resistance, herbicide tolerance, rooting ability, cold tolerance, drought tolerance, salinity tolerance, modified growth rate, modified fruit development, fruit with better appearance, fruit with better taste, fruit with better storage ability, fruit with better shelf life, and improved dried fruit.

According another embodiment, the exogenous polynucleotide transformed into the *Ficus* plant encodes a foreign protein. As used herein, the term "foreign protein" refers to a polypeptide or a protein not naturally present in the *Ficus* species to be transformed. According to one embodiment, the foreign protein is expressed in an edible part of the plant, specifically in the edible fruit of *Ficus carica*. As used herein, an edible fig fruit is defined as the multiple fruit developed from the complex fig inflorescence called synconium. The multiple fruit consist of fleshy receptacle surrounding by diminutive drupe that form from each pistillate flower. According to another embodiment, the foreign protein is expressed in the latex serum produced by the *Ficus* tree. The foreign protein may be utilized while maintained within the transgenic plant tissue, for example by consumption of transgenic edible *Ficus* fruit or by employing the latex serum. Alternatively, the foreign protein may be extracted from the transgenic *Ficus* plants.

According to one embodiment, the *Ficus* plant is the fig tree *Ficus carica* and the exogenous polynucleotide encodes a polypeptide contributing to the nutritional composition of the *Ficus carica* edible fruit.

According to another embodiment, the *Ficus* plant is the fig tree *Ficus carica* and the exogenous polynucleotide encodes a protein contributing to the therapeutic value of the *Ficus carica* edible fruit. Preferably, the protein is selected from the group consisting of an anti-cancer agent, an anti oxidant and a protein eliciting an immunogenic response in a mammal.

According to one embodiment, the present invention provides a transgenic *Ficus carica* plant producing fruit comprising at least one exogenous polynucleotide expressing one of the group consisting of a polypeptide, a functional portion of a polypeptide, a peptide, a protein and a fusion protein eliciting immunogenic response in a mammal, wherein the expression is at a level such that upon oral administration to a mammal, an immunogenic response is observed, thus forming an edible vaccine. The vaccine can be any vaccine as is known to a person skilled in the art, including but not limited to a vaccine for the treatment of hepatitis, malaria and cholera.

Pollen and ovules from the transgenic *Ficus* plants; the seeds produced from same and the plants grown from the seeds; edible fruit produced by the genetically modified plants; and plants regenerated from tissue cultures regenerated from the genetically modified plants of the present invention are also encompassed within the scope of the present invention.

According to yet another embodiment, the present invention provides a tissue culture regenerated from the transgenic *Ficus* plants of the present invention, wherein the tissue culture comprises cells or protoplasts from a transgenic tissue selected from the group consisting of leaves, pollen, embryos, roots, root tips, anthers, flowers, fruit and seeds.

According to another aspect, the present invention provides a method for producing transgenic *Ficus* species comprising:

a) transforming a genetic construct comprising at least one exogenous polynucleotide into at least one *Ficus* explant to form a putatively transformed explant;

b) inducing the regeneration of at least one adventitious shoot on the putatively transformed explant to obtain putatively transformed adventitious shoot;

c) selecting a transformed adventitious shoot; and d) culturing the transformed adventitious shoot to form a transgenic *Ficus* plantlet.

According to one embodiment, the explants are obtained from an in vitro *Ficus* culture. According to one currently preferred embodiment, the in vitro culture is prepared by horizontally placing shoot tips of *Ficus* on a solid propagation medium enabling shoot growth and leaf development. According to one embodiment, the propagation medium comprises at least one cytokinin, at least one auxin and optionally at least one gibberellin.

Techniques for transforming genetic constructs into the genome of target plants are well known in the art and include *Agrobacterium*-mediated introduction, electroporation, protoplast fusion, injection into reproductive organs, injection into immature embryos, high velocity projectile introduction, and the like. The choice of technique will depend upon the *Ficus* species to be transformed. Targets for the introduction of the genetic constructs of the present invention include tissues, such as leaf tissues, disseminated cells, protoplasts, seeds, embryos, meristematic regions, cotyledons, hypocotyls, and the like. According to one embodiment target plant material for transformation according to the methods of the present invention include explants obtained from in vitro cultures prepared as described above. The term "transformation" refers to the introduction of an isolated polynucleotide into a plant cell, either in culture or into the tissues of a plant.

According to one embodiment, transforming the explants is performed by co-culturing the explants with *Agrobacterium* culture harboring the genetic construct comprising the desired genetic material. The polynucleotide may integrate into the host cell genome ("stable transformation") or be expressed without such integration ("transient transformation"). According to one embodiment, co-culturing is performed with explants placed on a solid medium, abaxial side up. As used herein, the term "abaxial" refers to a surface facing away from the plant axis, as the lower side of a leaf; the term "adaxial" refers to a surface facing towards the plant axis, as the upper side of a leaf.

The present invention now discloses that surprisingly, transformation is highly dependent on the dorsoventral orientation of the explants.

*Agrobacterium*-mediated transformation occurs only when co-culturing is performed on a solid medium with the explants placed with their abaxial side up. No transformation is observed when the explants are placed adaxial side up.

According to one embodiment, the explants are wounded before culturing with *Agrobacterium*. According to one currently preferred embodiment, the *Agrobacterium* strain used is *Agrobacterium tumefaciens*. According to another embodiment, the co-culturing medium is a solid medium comprising at least one auxin and at least one cytokinin.

According to one embodiment, the *Ficus* explants taken for transformation are leaf explants. Fully developed leaves are excised from the in vitro shoot culture and taken for transformation.

The putatively transformed explants are transferred to conditions inducing the formation of adventitious shoots. According to one embodiment, the induction of adventitious shoots is obtained by placing the putatively transformed explants, adaxial side up, on a solid regeneration medium under low light intensity; transferring the explants to normal light intensity; and subsequently transferring the explants to a propagation medium under normal light intensity. As used herein "low light intensity" refers to light intensity from about 1 to about 5 $\mu mol/m^2$ s, and "normal light intensity" refers to light intensity from about 10 to about 60 $\mu mol/m^2$ s. According to one embodiment, the regeneration medium comprises at least one auxin, at least one cytokinin and at least one carbon source. According to another embodiment, the regeneration and the propagation media further comprise at least one selection agent. According to one currently preferred embodiment the selection agent is an antibiotic.

The frequency of shoot regeneration obtained by the method of the present invention, for wild type as well as transgenic *Ficus* species, is at least 80%, preferably 90%, more preferably 100%, with regeneration efficacy of at least 3 shoots per explant, preferably 5 shoots per explant, more preferably 10 shoots per explant. As used herein, the term "regeneration frequency" refers to the percentage of explants forming adventitious shoots. The term "regeneration efficacy" as used herein refers to the number of shoots regenerating on one explant. According to one currently preferred embodiment, the explants are leaf explants. After the development of adventitious shoots, only the transformed shoots are selected.

According to one embodiment the genetic construct of the present invention further comprises a selection marker conferring antibiotic resistance. The transformation method using a selection marker comprises:

a) exposing the putatively transformed explants to a regeneration medium comprising a first concentration of a first antibiotic and a second antibiotic, to obtain surviving regenerated shoots;

b) transferring the surviving shoots to a propagation medium comprising a second concentration of the first antibiotic and the second antibiotic;

c) repeating step (b); and d) transferring the surviving shoots of step (c) to the propagation medium comprising the second antibiotic.

According to one embodiment, the regeneration and propagation media are the media described herein above.

According to one embodiment, the second concentration of the first antibiotic is greater than its first concentration, and the concentration of the second antibiotic is constant. According to one currently preferred embodiment, the first antibiotic is kanamycin and the second antibiotic is ticarcillin.

Following selection of transformed shoots, the shoots are transferred to a rooting medium and roots are generated using techniques that are well known in the art. Rooted transgenic shoots, designated herein as transgenic plantlets, may be grown to mature transgenic *Ficus* plants. The plantlets include the genetic material introduced using the genetic construct according to the present invention. The products obtained from mature transgenic plants, including fruit, timber, latex serum, wood pulp, fuel wood, and the like, also contain the genetic modification.

The transformation and regeneration methods of the present invention provide means for the introduction of at least one exogenous polynucleotide into plants of the genus *Ficus*, specifically *Ficus carica*. The polynucleotide can be, for example, new gene, an additional copy of an existent gene, or a regulatory element. According to one embodiment, the transformation and regeneration methods of the present invention are utilized to introduce genetic material that confers desirable agronomical traits, selected from the group consisting of, but not limited to, insect tolerance, disease resistance, herbicide tolerance, rooting ability, cold tolerance, drought tolerance, salinity tolerance, modified growth rate, modified fruit development, fruit with better appearance, fruit with better taste, fruit with better storage ability, fruit with better shelf life, and improved dried fruit. According to this embodiment, the genetic material introduced may be homologous or heterologous to the genome of the target plant.

According to another embodiment, the transformation and regeneration methods of the present invention are utilized to introduce into *Ficus* plants at least one exogenous polynucleotide capable of expressing a foreign protein. Expression of the foreign protein can be constitutive or dependent upon induction, tissue specific or general. The Foreign protein can be extracted from the plant tissue for further purification and use, or can be used while maintained in the *Ficus* plant tissue. According to one embodiment, the foreign protein is expressed in an edible part of the plant, specifically in the edible fruit of *Ficus carica*.

According to one embodiment, the expressed foreign protein contributes to the nutritional composition and value of the fruit.

According to another embodiment, the expressed foreign protein contributes to the therapeutic value of the fruit. According to one currently preferred embodiment, the foreign protein is selected from the group consisting of an anti cancer agent, an anti oxidant and a protein eliciting an immunogenic response in a mammal.

According to one currently preferred embodiment, the transformation and regeneration methods of the present invention are utilized for the production of a transgenic *Ficus carica* producing fruit comprising protein eliciting immunogenic response in a mammal, wherein the protein is expressed in the plant at a level such that upon oral administration to a mammal, an immunogenic response is observed, thus forming an edible vaccine. The vaccine can be any vaccine as is known to a person skilled in the art, including but not limited to a vaccine for the treatment of hepatitis, malaria and cholera.

The present invention is better explained by the description, figures and claims that follow.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 8*a-b* show PCR analysis of genomic DNA isolated from putatively transgenic shoots of cv. Brown Turkey (A) and Smyrna (B). The transformed shoots showed the predicted bands of 645 bp for the npt II gene and of 676 bp for the uidA-intron (GUS).

FIG. 9 presents Southern analysis of genomic DNA isolated from putatively transformed shoot of fig cv. Brown Turkey and Smyrna. The transformed shoots showed the anticipated bands of the pME504 plasmid restriction map.

DETAILED DESCRIPTION OF THE INVENTION

Figure 1A:
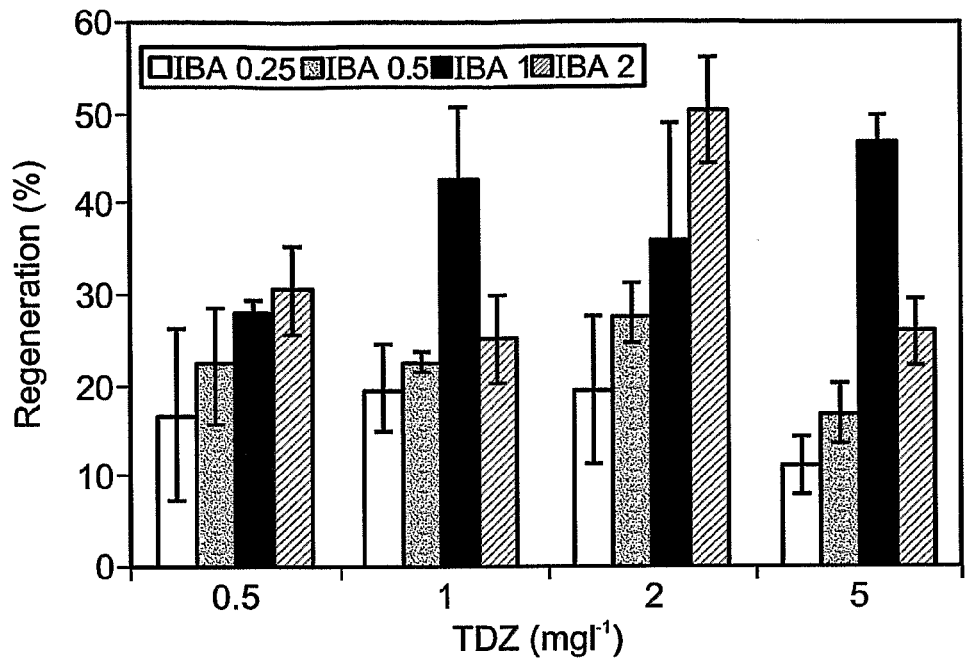
FIGS. 1*a-b* describe the effect of growth regulator concentration and light conditions on shoot regeneration of cv. Brown Turkey. Leaf explants were cultured with the abaxial side up following (A) one week low intensity light, (B) two weeks dark, one week low intensity light, and subsequently transferred to normal light. Vertical bars indicate standard error (±S.E.).

The present invention relates to genetically modified plants of the genus *Ficus*, and parts thereof, transformed with a genetic construct comprising at least one exogenous polynucleotide. The invention further relates to methods of (i) transforming *Ficus* explants and (ii) regenerating the transformed explants to obtain transgenic *Ficus* plants. The invention is also relates to products produced by or from the transgenic plants of the present invention. Specifically, the present invention relates to transgenic fig trees (*Ficus carica*), and to their use, inter alia, for the production of foreign proteins, as edible vaccines and as improved stocks for agronomical use.

According to the present invention, the genome of commercially valuable woody plants of the genus *Ficus* is modified by introducing at least one exogenous polynucleotide, either homologous or heterologous to the *Ficus* genome. The introduced polynucleotide can modify the production and/or function of a polypeptide of interest, for example increasing the amount of a rate-limiting enzyme by introducing additional copies of the gene. A reduction in the level of a polypeptide of interest can be achieved by transforming the target plant with at least one antisense copy of a gene encoding the polypeptide, or a functional portion thereof. Non-coding portions of polynucleotides, such as a regulatory polynucleotide and a polynucleotides encoding regulatory factor such as transcription factor, and/or functional portions of a transcription factor, and/or antisense copy of such a regulatory factor, can also be introduced to the target *Ficus* plants to modulate the expression of certain polypeptides. An exogenous polypeptide can also be introduced for the production of a foreign protein.

According to certain embodiments of the present invention, the introduced polynucleotide is expressed in a tissue specific manner to produce the foreign protein. According to one embodiment, the foreign protein is produced in an edible part of the plant, particularly in the fruit of *Ficus carica*. The fig tree is particularly advantageous as a species for production of foreign proteins due to the prolonged duration of ripening of the fruit on a single tree. Certain fig tree varieties, whether for use as a source of fresh fruit or dried fruit, have been developed to have fruit which are ripening during the course of months, and even the year round. This provides unique advantages for the use of figs as a species suitable for use for fruit-specific production of foreign proteins, and as edible vaccines. Foreign proteins to be produced by the transgenic fig tree are of nutritional and/or pharmaceutical value. As fig fruit are widely consumed, the genetically modified fruit can be used for administering nutritional and/or pharmaceutical compositions to animals and humans.

According to yet another embodiment, the foreign protein is expressed in the latex serum produced by *Ficus* species. The foreign proteins produced by the transgenic fig trees may be isolated from the plant tissue, or may be used while maintained within the plant tissue.

According to one aspect, the present invention provides transgenic *Ficus* species comprising a genetic construct comprising at least one exogenous polynucleotide. According to one embodiment, the *Ficus* species is *Ficus carica*.

The genetic material includes at least one exogenous polynucleotide desired to be introduced to the target *Ficus* plant. Genetic constructs introduced into the target plant may comprise a polynucleotide that is homologous and/or heterologous to the target plant genome, and may include polynucleotides encoding a polypeptide or a functional portion of a polypeptide, a polynucleotide encoding a regulatory factor, such as a transcription factor, a non-coding polynucleotides such as regulatory polynucleotides, and antisense polynucleotides that inhibit expression of a specified polypeptide. According to one embodiment, the genetic construct further comprises at least one regulatory element to confer functional expression of the exogenous polynucleotide in the *Ficus* plant. Expression of a polynucleotide refers to the process wherein a DNA region which is operably linked to appropriate regulatory element is transcribed into an RNA which is biologically active i.e., which is either capable of interaction with another nucleic acid or which is capable of being translated into a polypeptide or protein. As used herein, the term "polypeptide" encompasses amino acid chains of any length, including full-length proteins, wherein amino acid residues are linked by covalent peptide bonds.

According to one embodiment, the genetic construct according to the present invention is built in such a way to further include at least one marker gene conferring the ability to select transformed cells and tissues regenerated therefrom, for example callus, embryos and mature plants.

The transgenic *Ficus* plants of the present invention can be transformed with any polynucleotide of interest. As used herein "polynucleotide" means a polymeric collection of nucleotides and includes DNA and corresponding RNA molecules, both sense and anti-sense strands, and comprehends cDNA, genomic DNA and recombinant DNA, as well as wholly or partially synthesized polynucleotides. A polynucleotide may be an entire gene, or any portion thereof. Operable anti-sense polynucleotides may comprise a fragment of the corresponding polynucleotide, and the definition of "polynucleotide" therefore includes all such operable anti-sense fragments. Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthetic methods. All of the polynucleotides described herein are isolated and purified, as those terms are commonly used in the art.

When the genetic construct comprises a coding portion of a polynucleotide, the genetic construct further comprises a gene promoter sequence and a gene termination sequence operably linked to the polynucleotide to be transcribed. The gene promoter sequence is generally positioned at the 5' end of the polynucleotide to be transcribed, and is employed to initiate transcription of the polynucleotide. Promoter sequences are generally found in the 5' non-coding region of a gene but they may exist in introns or in the coding region. When the construct includes an open reading frame in a sense orientation, the gene promoter sequence also initiates translation of the open reading frame. For genetic constructs comprising either an open reading frame in an antisense orientation or a non-coding region, the gene promoter sequence may comprise a transcription initiation site having an RNA polymerase binding site.

A variety of gene promoter sequences that may be usefully employed in the genetic constructs of the present invention are well known in the art. The promoter gene sequence, and also the gene termination sequence, may be endogenous to the *Ficus* host or may be exogenous, provided the promoter is functional in species of the genus *Ficus*. For example, the promoter and termination sequences may be from other plant species, plant viruses, bacterial plasmids and the like.

The type of the requested expression will dictate the selection of a suitable promoter. The promoters may be constitutive, inducible, tissue-specific, or developmentally regulated. Promoter hybrids can also be constructed to enhance transcriptional activity (e.g., U.S. Pat. No. 5,106,739), or to combine desired transcriptional activity and tissue specificity.

Promoters often used for constitutive gene expression in plants include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter. A suitable inducible promoter may be selected from genes that are induced during a plant defense response against a parasite infection. For example, a fungal infection triggers an induction of a large number of pathogenesis-related (PR) proteins by the infected plant. The promoters of these PR sequences may be obtained and utilized in the present invention. Isolation of these PR promoters has been reported from potato plants (e.g., Matton, D. P. and Brisson, N. 1989. Mol Plant Microbe Interact. 2:325-31) and tobacco plants. Other inducible promoters are heat-shock promoters, a nitrate-inducible promoter derived from the spinach nitrite reductase sequence, hormone-inducible promoters, and light-inducible promoters associated with the small subunit of RuBP carboxylase and light harvesting chloroplast binding protein (LHCP) families.

According to one embodiment, the plant-expressible promoter is a tissue specific promoter. Using tissue specific promoters restricts the expression of the exogenous polynucleotide to the tissue where the promoter is operable. According to one currently preferred embodiment, the tissue specific promoter is specific to any one of the tissues forming the edible fig fruit.

The gene termination sequence, which is located 3' to the DNA sequence to be transcribed, may come from the same gene as the gene promoter sequence or may be the termination sequence of a different gene. Many gene termination sequences known in the art may be usefully employed in the present invention, such as the 3' end of the *Agrobacterium tumefaciens* nopaline synthase gene. However, preferred gene terminator sequences are those from the original polypeptide gene, or from the target *Ficus* species being transformed.

The genetic construct of the present invention can further comprise a reporter gene or a selection marker that is effective in the target plant cells to permit the detection of transgenic cells, tissues or plants containing the genetic construct. Such selection markers and reporter genes, which are well known in the art, typically confer resistance to one or more toxins and encode for a detectable enzymatic activity, respectively. The nptII gene, whose expression results in resistance to kanamycin or hygromycin antibiotics, which are generally toxic to plant cells at a moderate concentration, can be used as a selection marker as exemplified herein below. Alternatively, the presence of the desired construct in transgenic cells may be determined by means of other techniques that are well known in the art, including PCR, Southern and Western blots.

Techniques for operatively linking the components of the genetic constructs used to transform target plant materials are well known in the art and include the use of synthetic linkers containing one or more restriction endonuclease sites as described, for example, by Maniatis et al., (Molecular Cloning: A Laboratory Manual, Cold Spring Harbor Laboratories, Cold Spring Harbor, N.Y., 1989).

According to one embodiment, the transgenic *Ficus* plant of the present invention comprise a polynucleotide conferring a desirable agronomical trait selected from the group consisting of insect tolerance, disease resistance, herbicide tolerance, rooting ability, cold tolerance, drought tolerance, salinity tolerance, modified growth rate, modified fruit development, fruit with better appearance, fruit with better taste, fruit with better storage ability, fruit with better shelf life, and improved dried fruit.

As used herein, the term "storage ability" refers to the time period in which a fresh produce of a plant or parts thereof may be stored before marketing, under favorable conditions, without a significant decrease in its quality. The term "shelf life" as used herein refers to the time period in which a fresh produce of a plant or parts thereof may be stored on a market shelf without a significant decrease in its quality.

According another embodiment, the transgenic *Ficus* plant comprises a polynucleotide encoding a foreign protein. As used herein, the term "foreign protein" refers to a polypeptide or a protein not naturally present in the *Ficus* species to be transformed. According to one embodiment, the foreign proteins are expressed in an edible part of the plant, specifically in the edible fruit of *Ficus carica*. According to another embodiment, foreign proteins can be extracted from the transgenic *Ficus* plants.

The fig is particularly advantageous as a species for production of foreign proteins, specifically for the production of edible vaccines due to the prolonged duration of ripening of the fruit on a single tree, which, in few varieties, is during the year round. Thus, genetically modified fig trees can provide a constant supply of nutritionally valuable fruit and edible vaccines.

There are many examples of valuable proteins that are useful in pharmaceutical and industrial applications. Often these molecules are required in large quantities and in partially or highly purified formulations to maintain product quality and performance. Plants are an inexpensive source of proteins, including recombinant proteins. Methods for obtaining constitutive high expression of foreign proteins by plants and their extraction are known in the art (for example, U.S. Pat. Nos. 6,392,121 and 6,617,435, respectively).

According to one embodiment, the *Ficus* plant is the fig tree *Ficus carica* and the exogenous polynucleotide encodes a polypeptide contributing to the nutritional composition of the *Ficus carica* edible fruit.

According to another embodiment, the *Ficus* plant is the fig tree *Ficus carica* and the exogenous polynucleotide encodes a protein contributing to the therapeutic value of the *Ficus carica* edible fruit. Preferably, the protein is selected from the group consisting of an anti-cancer agent, an anti oxidant and a protein eliciting an immunogenic response in a mammal.

According to one currently preferred embodiment, the present invention provides a transgenic *Ficus carica* plant producing fruit comprising at least one exogenous polynucleotide expressing one of the group consisting of a polypeptide, a functional portion of a polypeptide, a peptide, a protein and a fusion protein eliciting immunogenic response in a mammal, wherein the expression is at a level such that upon oral administration to a mammal, an immunogenic response is observed, thus forming an edible vaccine.

Vaccines are administered to human and animal to induce their immune system to produce antibodies against viruses, bacteria and other types of pathogenic microorganisms. Thus, vaccination prevents the occurrence, or reduces severity of a disease once the body is attacked by such pathogens. Diseases like smallpox have been practically disappeared due to the development of immunization program. However, many vaccines for diseases as poliomyelitis, measles, mumps, rabies, foot and mouth, and hepatitis B are still too expensive for the lesser-developed countries to provide to their large human and animal populations, as these countries do not have the monetary funds to immunize their populations with currently available vaccines. The immunization cost includes not only the cost of producing the vaccine but the further cost of the professional administration, particularly as some vaccines require multiple doses to maintain immunity. Therefore, often, the countries that need the vaccines the most can afford them the least. It has been previously shown that plants can be transformed and efficiently express immunogenic protein in an amount sufficient for protein purification and vaccine production as well as for eliciting immunogenic response in a mammal consuming the transgenic plant or parts thereof. Genetic constructs for tissue specific expression are known in the art, thus the immunogenic proteins can be expressed specifically in the plant edible parts. Fig fruit, which are consumed for their nutritional value can therefore provide inexpensive and highly accessible source for various vaccines. Thus, the oral vaccines produced by the transgenic plants of the present invention are preferably administered by the consumption of the fruit produced by the transgenic plant. However, immunogenic compositions derived from the transgenic plant materials suitable for use as more traditional immune vaccines may be also readily prepared from the transgenic plant materials described herein. Preferably, such immune compositions will comprise a material purified from the transgenic plant. Purification of the antigen may take many forms as is known to those of skill in the art. Whatever initial purification scheme is utilized, the purified material will also be extensively dialyzed to remove undesired small molecular weight molecules (i.e., sugars, pyrogens) and optionally lyophilized for more ready formulation into a desired vehicle.

The vaccine can be any vaccine as is known to a person skilled in the art, including but not limited to a vaccine for the treatment of hepatitis, malaria, and cholera.

Pollen and ovules from the transgenic *Ficus* plants; the seeds produced from same and the plants grown from the seeds; edible fruit produced by the genetically modified plants; and plants regenerated from tissue cultures regenerated from the genetically modified plants of the present invention are also encompassed within the scope of the present invention.

According to yet another embodiment, the present invention provides a tissue culture regenerated from the transgenic *Ficus* plants of the present invention, wherein the tissue culture comprises cells or protoplasts from a tissue selected from the group consisting of leaves, pollen, embryos, roots, root tips, anthers, flowers, fruit and seeds.

According to another aspect, the present invention provides a method for producing genetically modified *Ficus* species comprising:

a) transforming a genetic construct comprising at least one exogenous polynucleotide into at least one *Ficus* explant to form a putatively transformed explant;

b) inducing the formation of at least one adventitious shoot on the putatively transformed explant to obtain putatively transformed adventitious shoot;

c) selecting transformed adventitious shoot; and d) culturing the transformed adventitious shoot to form a transgenic *Ficus* plantlet.

According to one embodiment the methods of the present invention employ in vitro fig shoot cultures as a starting material from which the explants are obtained. Preparation of shoot cultures is known in the art (for example, Pontikis and Melas, 1986. Hort Science 21/1, pp. 153). Briefly, cultures are initiates from shoot tips. The elongated shoots are grown on a solid propagation medium until leaves are developed. According to one embodiment, the shoots are placed on a solid propagation medium in a horizontal position in a Magenta box, with multiple shoots per box. In addition to a basal salt mixture the medium comprises at least one auxin, at least one cytokinin and optionally at least one gibberellin. Typically, the basal salt mixture used is full strength MS (Murashige and Skoog) medium, the auxin is indol-3-butyric acid (IBA), the cytokinin is 6-benzylaminopurine (BA) the gibberellic acid is $GA_3$. The medium typically further comprises sucrose as a carbon source. The medium further comprises myoinositol and thiamine-HCl and the pH of the medium is kept in the range of from about 4.5 to about 6.5.

The cultures are exposed to a cool fluorescent light in a photoperiod of 16 h of light and 8 h dark, at 25° C. Typically, the light intensity is in the range of between 30 to 50 $\mu mol/m^2$ s. Under theses conditions (the propagation medium and the light regime) elongation of the micropropagating shoots and the formation of leaves from the shoot buds occur within about four to five weeks.

In the last two decades, transformation technology has played an increasingly important role in the genetic manipulation of crop plants for their improvement and the study of the molecular mechanisms underlying plant gene expression and regulation. However, due to the lack of a useable transformation and regeneration procedure, the application of such biotechnological approaches has not been possible for species in the genus *Ficus*. Successful transformation of *Ficus* cells using transformation procedures as described herein, and the subsequent regeneration of transgenic plants, provide a new mean for the introduction of foreign genes into *Ficus* species, specifically into the commercially valuable fig tree (*Ficus carica*). This technology enables the development of transgenic *Ficus* varieties with improved agronomic performance characteristics, provides a new experimental system for study of gene expression and function in these species, and provides a mean for the production of foreign proteins in edible parts of *Ficus* species, specifically the production of edible vaccines. The use of *Ficus carica* varieties improved via the utilization of the transformation and regeneration technology of the present invention also facilitates the implementation of sustainable agricultural practices in fig tree cultivation.

Methods for polynucleotide transfer into a plant cell are known in the art, and include, inter alia, *Agrobacterium*-mediated introduction, protoplast fusion, viral-mediated transformation, high velocity projectile introduction, electroporation, injection into reproductive organs, and injection into immature embryos.

The probably most common method utilized for plants is *Agrobacterium*-mediated transformation. In addition, additional methods defined as "direct" gene transfer procedures have been developed to transform plants and plant tissues without the use of an *Agrobacterium* intermediate. Plant regeneration from protoplasts is a particularly useful technique (Evans, D. A. et al., 1983. Handbook of Plant Cell Culture 1, 124). When a plant species can be regenerated from protoplasts, direct gene transfer procedures can be utilized and transformation is not dependent on the use of *Agrobacterium*. In the direct transformation of protoplasts the uptake of exogenous genetic material into a protoplast may be enhanced by use of a chemical agent (for example Polyethylene glycol) or electric field (electroporation). The exogenous material may then be integrated into the nuclear genome. Alternatively, genetically modified plants may be obtained by fusion of two distinct protoplasts carrying different genetic material followed by regeneration of the fused protoplast.

DNA viruses have been also used as gene vectors in plants. For example, a cauliflower mosaic virus carrying a modified bacterial methotrexate-resistance gene was used to infect a plant, and the foreign gene was systematically spread in the plant. The advantages of this system are the ease of infection, systematic spread within the plant, and multiple copies of the gene per cell.

A recently developed procedure for direct gene transfer involves bombardment of cells by microprojectiles carrying DNA (Klein, T. M. et al., 1987. Nature 327:70-72). In this "biolistic" procedure, tungsten or gold particles coated with the exogenous DNA are accelerated toward the target cells. Transient as well as stable expression has been achieved using this procedure (Klein, T. M. et al., 1992. Bio/Technology 10: 286-291).

According to one embodiment, transforming the genetic construct according to the present invention is performed by co-culturing the at least one explant with *Agrobacterium* harboring the genetic construct comprising the desired exogenous polynucleotide such that the genetic construct is transformed into the explant.

The term "*Agrobacterium*" refers to a soil-borne, Gram-negative, rod-shaped phytopathogenic bacterium, which causes crown gall. The term "*Agrobacterium*" includes, but is not limited to, the strains *Agrobacterium tumefaciens*, (which typically causes crown gall in infected plants). Infection of a plant cell with *Agrobacterium* generally results in the production of opines (e.g., nopaline, agropine, octopine etc.) by the infected cell. Thus, *Agrobacterium* strains which cause production of nopaline (e.g. strain LBA4301, C58, A208) are referred to as "nopaline-type" *Agrobacteria*; *Agrobacterium* strains which cause production of octopine (e.g. strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria*. Any *A. tumefaciens* strain harboring a disarmed Ti plasmid may be used in the methods of the invention utilizing any available *Agrobacterium* system may be used. For example, Ti plasmid/binary vector system or a co-integrative vector system with one Ti plasmid may be used. According to one embodiment, *A. tumefaciens* strain EHA105 is used according to the methods of the present invention.

Colonies of *Agrobacterium* carrying the genetic construct of interest are prepared for inoculating the explants using methods which are well known to one skilled in the art, as exemplified herein below. Explants taken from in vitro shoot cultures as described above are selected for transformation. According to one embodiment, the explants are lead explants. Before inoculating the explants with *Agrobacterium* the explants are wounded; typically, when leaf explants are used, the leaves are wounded across the midrib. The terms "wounded" or "wounding" as used herein refers to the introduction of a wound in the plant tissue. Wounding of plant tissue may be achieved, for example, by punching, by using a blade, by maceration etc.

Inoculation of explants with the *Agrobacterium* suspension takes place under conditions that optimize infection of the explants. According to one embodiment, the explants are immersed in the *Agrobacterium* suspension for at least about twenty minutes, at a temperature of about 22° C. to 30° C. After incubation, excess suspension is removed and explants are transferred to a solid co-cultivation medium. The explants are placed on the medium with their upper side facing the medium (abaxial side up). The present invention now discloses that transformation is completely dependent on the orientation in which the explants are placed on the medium during co-cultivation, i.e. no transformation occurs when the explants are placed in the opposite orientation (adaxial side up).

According to another embodiment, the co-culturing medium comprises at least one auxin and at least one cytokinin. According to one embodiment, the auxin is selected from indole-3-butyric acid (IBA) and 2,4-dichlorophenoxy acetic acid (2,4-D) and the cytokinin is thidiazuron (N-phenyl-N'-1,2,3-thiadiazol-5-yl urea, TDZ).

According to one embodiment, co-cultivation is performed for a period of from about 65 h to about 80 h in the dark at a temperature range of 22° C.-28° C. After co-cultivation with *Agrobacterium*, putatively transformed explants are transferred to a fresh medium to induce the formation of adventitious shoots and selection of transformed shoots.

Transformation of a cell may be stable or transient. The term "transient transformation" or "transiently transformed" refers to the introduction of one or more exogenous polynucleotides into a cell in the absence of integration of the exogenous polynucleotide into the host cell's genome. Transient transformation may be detected by, for example, enzyme-linked immunosorbent assay (ELISA) which detects the presence of a polypeptide encoded by one or more of the exogenous polynucleotides. Alternatively, transient transformation may be detected by detecting the activity of the protein (e.g. β-glucuronidase) encoded by the exogenous polynucleotide. The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences. The term "stable transformant" refers to a cell which has stably integrated one or more exogenous polynucleotides into the genomic or organellar DNA.

According to one embodiment, the explants removed from the co-cultivation medium are first washed. A preferred washing medium comprises MS medium comprising the antibacterial antibiotic ticaracillin, preferably at a concentration of from about 250 mg/l to 350 mg/l, to eliminate the *Agrobacterium*. The putatively transformed explants are then transferred to a fresh, solid regeneration medium under conditions which promotes bud regenerating and shoot formation. According to one embodiment, the regeneration medium further comprises at least one selection agent. According to one currently preferred embodiment, the regeneration medium is based on MS medium comprising at least one auxin, at least one cytokinin and at least one carbon source, further comprising at least two selection agents.

The success of gene transfer techniques is largely dependent on efficient regeneration system. Hitherto, only Yakushiji et al. (supra) have reported a successful regeneration of *Ficus carica*; however, a regeneration frequency of about only 22% obtained by the methods described therein is not sufficient for production of transgenic *Ficus* plants.

The present invention discloses a highly efficient system for in vitro regeneration of non-transformed as well as transformed species within the genus *Ficus*, specifically of fig tree (*Ficus carica* L.), showing for the first time regeneration frequency of at least 80%, preferably 90%, more preferably 100%. Without wishing to be bound to a specific mechanism, a key factor in the high efficacy of both, transformation and shoot regeneration is the dorsoventral orientation of the explants, specifically leaf explants. In contrast to transformation, the high regeneration frequency is obtained when explants are put on the solid regeneration medium with their adaxial side up. When the explants are put with abaxial side up, although regeneration of shoots is observed, regeneration is apparent only on the free adaxial surface loosing contact with the medium. The difference in the regeneration rate may be due to the morphological differences between the adaxial and abaxial epidermal layers, requiring different threshold levels of hormones for regeneration. In addition, a regeneration efficacy of at least 3, preferably 5, more preferably 10 shoots per regenerating explant, is also observed using the methods of the present invention.

According to one embodiment, the auxin in the regeneration medium is IBA at a concentration in the range of 1-3 ppm; the cytokinin is TDZ in a concentration range of 1-3 ppm; and the carbon source is sucrose in a concentration range of from about 2% to 6% (w/w). As exemplified herein below, this combination of growth regulators and carbon source confer optimal shoot regeneration from the transformed leaf explants of *Ficus carica*. The putatively transformed explants are grown under low light intensity for about one week and are then transferred to normal light intensity. After a growth period of from about 3 weeks to about 10 weeks bud regeneration and adventitious shoot formation is observed. During this growth period, the regenerating shoots are transferred to a propagation medium. According to one embodiment, the putatively transformed explants are grown under low light intensity of from about 1 to about 5 $\mu mol/m^2$ s and under normal light intensity of from about 10 to about 60 $\mu mol/m^2$ s.

During the process of regeneration and development, transformed adventitious shoots containing the genetic construct are selected.

According to one embodiment the genetic construct of the present invention comprises a selection marker conferring antibiotic resistance. The transformation using a selection marker comprises:

a) exposing the putatively transformed explants to a regeneration medium comprising a first concentration of a first antibiotic and a second antibiotic, to obtain surviving regenerated shoots;

b) transferring the surviving shoots to a propagation medium comprising a second concentration of the first antibiotic and the second antibiotic;

c) repeating step (b); and d) transferring the surviving shoots of step (c) to the propagation medium comprising the second antibiotic.

According to one embodiment, the regeneration and propagation media are the media described above.

According to one embodiment, the second concentration of the first antibiotic is greater than its first concentration, and the concentration of the second antibiotic is constant. According to another currently preferred embodiment, the first concentration of the first antibiotic is 50 mg/l, the second concentration of the first antibiotic is 100 mg/l and the concentration of the second antibiotic is 150 mg/l. According to one currently preferred embodiment, the first antibiotic is kanamycin and the second antibiotic is ticarcillin. This four-stage selection method substantially eliminates the presence of chimeric shoots in the selected transformed shoots and prevents deleterious side effects of the antibiotics. When *Agrobacterium*-mediated transformation is employed, the presence of ticarcillin removes the remaining of *Agrobacterium*.

Transformed shoots are transferred to a suitable rooting medium. Rooting media and methods of rooting are known to one skilled in the art. According to one embodiment, the root induction medium of the present invention comprises half concentration MS medium supplemented with myo-inositol, thiamine HCl, phloroglucinol, and sucrose, at pH 5.7. The transformed shoots are transferred directly from the regeneration/selection medium to rooting cylinders with soil mixture moistened with root induction medium, wherein the medium optionally comprises 1 mg/l auxin, preferably IBA. Rooting is accomplished in a period of 10-30 days. According to one embodiment, plantlets are first kept under high humidity conditions of 50-80% and are then transferred for acclimatization and hardening by a stepwise decrease of the relative humidity. However, the transformed shoots can generate healthy root system when kept directly in ambient air conditions. Rooting efficacy (the percentage of transformed shoots which develop healthy root system) according to the present invention is at least 85%, preferably 95%, more preferably 100%. Transformed plantlet may be grown to produce genetically modified mature plants.

According to one embodiment, the transformation and regeneration methods of the present invention are utilized to introduce genetic material that confers desirable agronomical traits, including, but not limited to insect tolerance, disease resistance, herbicide tolerance, rooting ability, cold tolerance, drought tolerance, salinity tolerance, modification of growth rates and properties, fruit with better appearance, fruit with better taste, fruit with better storage ability, fruit with better shelf life, and improved dried fruit. According to this embodiment, the genetic material introduced may be homologous or heterologous to the genome of the target plant. Introducing new traits to an existing plant variety by traditional breeding methods is a time and work consuming process, even for herbaceous plants and moreover for woody plants having a life cycle of years. In *Ficus carica*, using the traditional genetic manipulation is even more complicated, as some trees bear only female synconium and others, named caprifig, bear both male and female flowers. True fruits can be produced only on tress bearing female synconium only. In nature, cross-pollination is mediated by a specific wasp. Thus traits donated by the stamens are hard to track and artificial pollination is hard to manipulate.

The origin of fig (Ficus *carica*, Moraceae) is tracked to Western Asia, from where it was spread to the Mediterranean. As of toady, fig trees are cultivated in many locations with an estimated annual production of one million tons of fruit grown mainly in Turkey and Egypt and also in Morocco, Spain, Greece, California, Italy, Algeria, Syria and Tunisia. Approximately 40% of the fig crop is sold as dried fruit, with the remainder dividing between fresh produce, paste, juice and canned preserves. Dried and processed figs not suitable for human consumption can be used as animal fodder. The nutritional value of fresh figs is comparable to that of many other fruits. They are high in calcium. Dried figs, with only 20% water are nutritious relative to other fresh fruits There are two main commercial types of figs, the "common fig" that produces fruit without pollination, and the "Smyrna fig" that requires pollination by a fig wasp (*Blastophaga* spp.), that lives in the "caprifig" (male fig), to set fruit. The "common-type" (self-pollinated) fig is more commonly grown. These cultivars bear one or two crops per year. The economic importance of fig production is likely to continue into the future. Worldwide, there is an increasing demand for fresh figs and a stable demand for dried figs. However, the short storage and shelf life of fresh fruit, and lack of improved agricultural varieties limits the commercial growth of fig trees.

According to another embodiment, the transformation and regeneration methods of the present invention are utilized to introduce heterologous genetic material for the production of foreign proteins by *Ficus carica*. The foreign proteins to be produced by such genetically modified plants are proteins that can modulate the nutritional composition and value of the edible fig fruit. According to one currently preferred embodiment, the introduced foreign protein is an anti-oxidant.

According to yet another embodiment, the transformation and regeneration methods of the present invention are utilized to introduce heterologous genetic material for the production of vaccines, particularly to the production of vaccines by the edible fruit of the fig trees.

According to another aspect, the present invention provides genetically modified *Ficus* species, specifically *Ficus carica* plants and parts thereof stably transformed with a genetic construct comprising at least one polynucleotide of interest. Plants and parts thereof propagated from the genetically modified *Ficus* plants; Pollen and ovules from the genetically modified *Ficus* plants; the seeds produced from same and the plants grown from the seeds; fruit produced by these plants; and plants regenerated form tissue cultures regenerated from the plants of the present invention are also encompassed within the scope of the present invention.

According to yet another embodiment, the present invention provides a tissue culture regenerated from the genetically modified *Ficus* plants of the present invention, wherein the tissue culture comprises cells or protoplasts from a tissue selected from the group consisting of leaves, pollen, embryos, roots, root tips, anthers, flowers, fruit and seeds.

According to one embodiment, the genetically modified *Ficus* species are produced by the transformation and regeneration methods of the present invention.

According to yet another aspect, the present invention provides a genetically modified *Ficus* plant wherein the plant is transformed with a genetic construct comprising polynucleotide encoding for at least one protein that is heterologous to the genome of the *Ficus* plant.

According to one embodiment, the present invention provides *Ficus carica* plants stably transformed with a genetic construct comprising polynucleotide encoding for at least one polynucleotide, said polynucleotide encodes for a protein contributing to the nutritional value of the *Ficus carica* edible fruit. According to one currently preferred embodiment, the protein is an anti-oxidant. According to one currently preferred embodiment, the protein is an anti-cancer agent.

According to another embodiment, the genetically modified plant of the present invention expresses at least one protein that can elicit an immunogenic response in a mammal. Preferably, the protein eliciting the immunogenic response is expressed in an edible part of the plant, specifically in the fruit. According to one currently preferred embodiment, the present invention provides a genetically modified *Ficus carica* plant producing fruit comprising protein eliciting immunogenic response in a mammal, wherein the protein is expressed in the fruit at a level such that upon oral administration to an animal, an immunogenic response is observed, thus forming an edible vaccine.

The transformation and regeneration methods of the present invention can be used to produce any type of vaccine effective in immunizing humans and animals against diseases. Viruses, bacteria, fungi, and parasites that cause diseases in humans and animals can contain antigenic protein(s) which can confer immunity in a human or an animal to the causative pathogen. A DNA sequence coding any of this viral, bacterial, fungal or parasitic antigenic protein may be used in the present invention. Mutant and variant forms of the DNA sequences encoding an antigenic protein which confers immunity to a particular virus, bacteria, fungus or parasite in a mammal (including humans) may also be utilized in this invention. For example, expression vectors may contain DNA coding sequences which are altered so as to change one or more amino acid residues in the antigenic protein expressed in the plant, thereby altering the antigenicity of the expressed protein. Expression vectors containing a DNA sequence encoding only a portion of an antigenic protein as either a smaller peptide or as a component of a new chimeric fusion protein are also included in this invention.

As explained herein above, the production of the immunogenic protein is directed to the fruit to produce edible vaccine, thus the genetic construct to be used for producing the vaccine comprises a fruit specific promoter, operably linked to a polynucleotide encoding the immunogenic protein. According to the present invention, any *Agrobacterium* delivery system may be employed to transform *Ficus carica* with the genetic construct.

The present invention allows for the production of not only a single vaccine in the *Ficus carica* fruit but for a plurality of vaccines. Polynucleotides coding for multiple antigenic proteins can be included in the genetic construct, thereby casing the expression of multiple antigenic amino acid sequences in one transgenic plant. Alternatively, a plant may be sequentially or simultaneously transformed with a series of genetic constructs, each of which contains DNA segments encoding one or more antigenic proteins. For example, there are five or six different types of influenza, each requiring a different vaccine. A transgenic plant expressing multiple antigenic protein sequences can simultaneously elicit an immune response to more than one of these strains, thereby giving disease immunity even though the most prevalent strain is not known in advance.

The vaccine produced by the genetically modified *Ficus* plants according to the present invention can be any vaccine as is known to a person skilled in the art. According to one embodiment, the vaccine is selected from the group consisting of a vaccine for hepatitis, malaria and cholera.

The principles of the invention, providing efficient transformation and regeneration methods for the production of genetically modified *Ficus carica* plants according to the present invention, may be better understood with reference to the following non-limiting examples.

EXAMPLES

Materials and Methods

Fig Shoot Culture Maintenance

Fig (Ficus *carica* L.) cultivars Brown Turkey (common for obtaining fresh produce) and Smyrna (common for dry fruits production) were used. In vitro shoot cultures of both cultivars were established according to Pontikis and Melas (supra) and subsequently grown on proliferation medium (PM) consisted of MS (Murashige and Skoog, 1962. Physiol. Plant. 15, 473-497) basal salt mixture supplemented with 100 mg/l myo-inositol, 0.5 mg/l thiamine-HCl, 3% sucrose (w/v), 0.8% agar (Sigma) and addition of 0.25 mg/l BA, 0.05 mg/l IBA and 0.05 mg/l $GA_3$. The pH was adjusted to 5.7 prior to (40 μmol/m$^2$ s) in a 16 hL/8 hD photoperiod at 25° C. for 4-5 weeks before the leaf explants were removed.

Plant Regeneration

Regeneration experiments were carried out initially with the cultivar Brown Turkey. To examine the effect of culture media on adventitious bud formation, the basal media MS, AP [13] and NN [14]; and various combinations of the auxins IBA and NAA (0.25-2 mg/l), NAA with the cytokinins TDZ (0.5-5 mg/l) and BA (2-5 mg/l) were examined. A control treatment with only TDZ (0.5-5 mg/l) was performed. The regeneration media contained MS basal salt mixture, supplemented with 100 mg/l myo-inositol, 1 mg/l thiamine-HCl, 2-4% sucrose (w/v) and 0.8%, agar (Sigma), at pH 5.7. The effect of the addition of 0.25% activated charcoal (AC) was also examined.

The youngest three expanded leaves isolated from 3-4 weeks old plants were used as explants. Each leaf was wounded forming three scares perpendicular to the central vein and placed on regeneration medium with the abaxial or adaxial surface down. Minimum ten Petri dishes, each containing ten explants were used per treatment. The cultures were kept for 7 days in low light intensity (2.5 μmol/m$^2$ s) followed by exposure to high light intensity (40 μmol/m$^2$ s) at 25° C., in a 16 hL/8 hD photoperiod. Leaf explants were examined after 28 and 35 days and the percentage of explant producing shoots (regeneration capacity) and the mean of adventitious shoots formed per regenerating explant (regeneration efficacy) were recorded. All experiments were repeated at least three times.

Rooting and Acclimatization

Two methods for rooting were examined. According to one method, each shoot was cultivated individually in a tube with root induction (RI) medium composed of half concentration MS medium (½MS) supplemented with 100 mg/l myo-inositol, 1 mg/l thiamine-HCl, 90 mg/l phloroglucinol, 2% sucrose (w/v), 0.25% activated charcoal (AC) and 0.8% agar (pH=5.7). The effect of IBA at different concentrations (0, 1, 2 mg/l) was also tested. Each treatment included 32 individual plants. According to another method, well developed shoots (up to 3-4 cm long with 3-4 expanded leaves) were directly transplanted from the proliferation medium to Rooting Cylinders (3.5 cm high×3.0 cm in diameter) with soil mixture comprising 55% granular polypropylene foam, 30% peat and 15% perlite (Tivonchem Ltd, Israel) moistened/soaked/with liquid RI medium without AC, supplemented with either 0, 1, 2 mg/l IBA. Results were scored (0=shoot with no root; 1=rotting shoot) after 4 weeks and based on 32 shoots (8 Magenta boxes with 4 cylinders) per treatment. Each experiment was repeated three times. Plantlets were cultured in closed boxes for one week in a growth chamber and then transferred for one week to a greenhouse. Then the plantlets were further transferred to a high humidity chamber without closures for additional 2 weeks for further acclimatization by decreasing the relative humidity stepwise.

Histology

The regeneration process was examined by light microscopy. Samples were fixed in a solution of freshly prepared FAA (Formal Acetic Alcohol), dehydrated in a graded ethanol series and embedded in Paraplast. Sections were cut at 10 mm thickness, stained in Safranin and Fast-Green, mounted in Permount (Fisher) and examined, using Leica DMLB light microscope.

Agrobacterium tumefaciens Strain and Plasmid

Supervirulent Agrobacterium tumefaciens strain EHA 105 (Hood et. al., 1993. Transgen. Res. 2, 208-218) harboring the vector pME 504 carrying the nptII, and the uidA-intron genes (Vancanneyt et al., 1990. Mol. Gen. Genet. 220, 245-250) was used. Agrobacterium culture was grown overnight in LB medium (Duchefa L-1704) with appropriate antibiotics. Bacteria were spun down by centrifugation (4000 rpm for 15 min), resuspended in liquid SIM medium (Alt-Möerbe et al., 1989. MPMI 2, 301-308) supplemented with 100 μM Acetosyringone (AS) to obtain a final $OD_{600}$ of 0.7, and incubated in orbital shaker for 4 h at 28° C. and 250 rpm, After the incubation, the Agrobacterium culture was ready for use as an inoculum.

Transformation

The leaves of 3-4 weeks old micropropagated shoots were wounded across the midrib with a scalpel and immersed in the bacterial suspension for 20 min, blotted on filter paper and cultured on regeneration medium based on MS medium and supplemented with 2.0 mg/l TDZ and 2 mg/l IBA, 4% sucrose, 0.8% agar and pH 5.7. Co-cultivation medium was supplemented with 100 μM AS. After co-cultivation period of 72 hours in the dark at 25° C.±1 the explants were washed in liquid MS medium with 300 mg/l ticarcillin, blotted dry and transferred to the regeneration medium with addition of ticarcillin (150 mg/l) and kanamycin (50, 75 and 100 mg/l). The effect of paromomycin (25 and 50 mg/l) as selective agent also was tested.

In order to increase the efficiency of the selection a set of additional experiments was performed. Following co-cultivation with Agrobacterium tumefaciens on solid medium the explants were cultured for 0, 3, 7 and 10 days in liquid regeneration medium containing 50 mg/l kanamycin and ticarcillin (150 mg/l). Ten leaves were placed in 10 ml liquid selection medium with addition of 0.5 ml Amberlite XAD-7 (Sigma) in Erlenmeyer (100 ml) in orbital shaker (85 rpm). Amberlite was sterilized by immersing in 70% ethanol overnight, washed three times by sterile water and mixed with equal portion (w/v) liquid selection medium. The liquid selection medium and amberlite were changed every 3 days. Then the explants were blotted dry and transferred to solid selection medium with 100 mg/l kanamycin and ticarcillin (150 mg/l) for the completion of total of four weeks. A control treatment with leaf explants transferred directly to solid medium with 100 mg/l kanamycin and 150 mg/l ticarcillin was also performed. Each treatment was designed in five replications and the experiment was repeated twice.

All cultures were kept during the first week in low light intensity (2.5 μmol/m$^2$ s) and subsequently transferred for the next 3 weeks to fluorescent light (40 μmol/m$^2$ s), in 16 hL/8 hD photoperiod at 25° C.±1. Regenerated shoots were developed after two subcultures in propagation medium (PM) supplemented with 100 mg/l kanamycin and 150 mg/l ticarcillin. Transformation frequency was counted as the number of independent transformation events (kanamycin resistant/GUS expressing shoots) obtained from the total number of explants.

Multiplication and maintenance of the selected plants were performed by culturing the shoots horizontally on PM with kanamycin (50 or 100 mg/l) and ticarcillin (150 mg/l) as individual clones. Rooting procedure was carried out in rooting cylinders soaked with the liquid medium described above, containing 100 mg/l kanamycin. Acclimatization of the rooted plantlets to the greenhouse conditions was performed by progressively decreasing the relative humidity within 3-4 weeks.

Molecular Confirmation of Transformation

All selected clones were subjected to molecular analyses by PCR and Southern blotting for the presence and integration of the nptII and GUS genes. Plant genomic DNA was isolated from the youngest three leaves excised from kanamycin resistant shoots according to Murray and Tompson (1980. Nucl Acids Res 8, 4321-4325).

The oligonucleotide primers used for the PCR amplification of a 645 bp fragment of the nptII gene were:

```
221924-Direct primer
5'-GCC GCT TGG GTG GAG AGG CTA T-3'   (SEQ ID NO: 1)
(63.6° C.);
and 221925-Reverse primer
5'-GAG GAA GCG GTC AGC CCA TTC-3'     (SEQ ID NO: 2)
(60° C.).
```

The primers for a 676 bp fragment of the GUS gene were:

```
17081-001-GUSup
5'-CGA GCG ATT TGG TCA TGT GAA G-3'   (SEQ ID NO: 3)
(57.5° C.);
and 17081-002-GUSlow primer
5'-CAT TGT TTG CCT CCC TGC TGC GGT    (SEQ ID NO: 4)
T-3' (55.9° C.) (Sigma).
```

Amplification was performed in aliquots of 25 µl using a thermal cycler (Biometra). The PCR conditions for amplification of the nptII gene fragment were 95° C. for 5 min, followed by 35 cycles at 94° C. for 1 min, 62° C. for 1 min, 72° C. for 1 min, and a final extension at 72° C. for 10 min. Amplification of the uidA-intron fragment was performed with the following program: 95° C. for 5 min followed by 35 cycles at 94° C. for 45 s, 55° C. for 45 s, 72° C. for 45 s, and a final extension at 72° C. for 10 min.

For the Southern blot analysis, 10 µg of genomic DNA was digested with the enzyme HindIII, subjected to electrophoresis on 0.8% agarose gel and transferred to nylon membranes (GeneScreen Plus, NEN, Boston, Mass.). Southern hybridization was performed using a [$^{32}$P]-radioactively labeled 524-bp nptII gene fragment as a probe, as described The membrane was washed at high-stringency conditions in a buffer consisting of 0.1×SSC, and 0.5% SDS at 65° C.

Histochemical GUS Assay

Histochemical analysis was performed following the procedure of Jefferson et al. (1987. EMBO J. 6, 3901-3907).

Transient GUS expression was assayed four and seven days after infection. Regenerating leaf explants cultivated four weeks in selective conditions of kanamycin (50 mg/l) and ticarcillin (150 mg/l) were also tested for β-glucuronidase activity. GUS expression was also examined in putatively transformed shoots and in rooted plantlet selective conditions.

Example 1

Plant Regeneration

Effect of the Growth Regulators

Figure 1B:
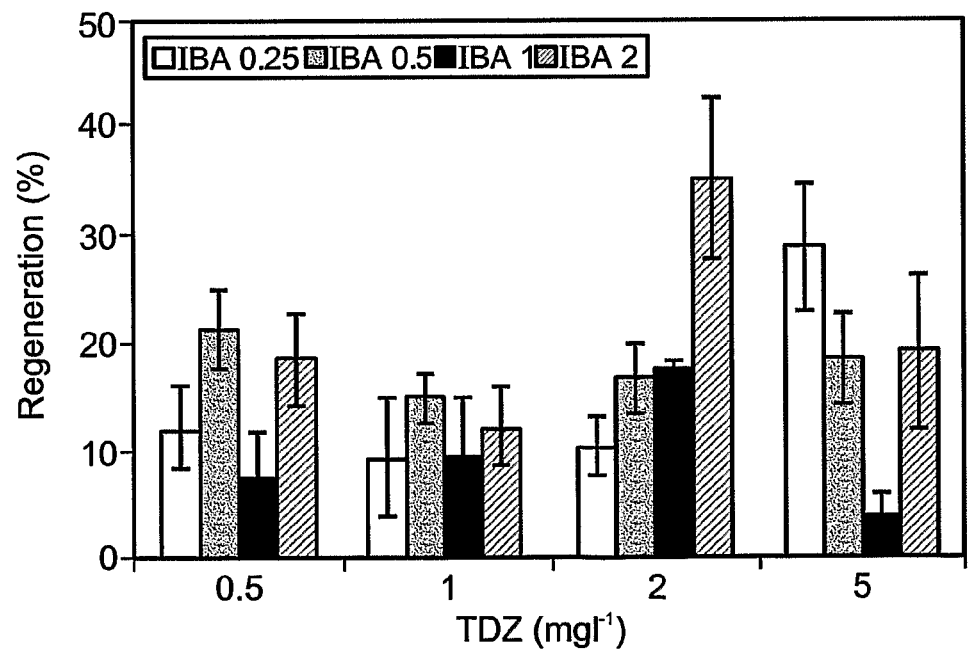

Our preliminary experiments have shown that use of MS basal medium supplemented with a combination of IBA and TDZ resulted in shoot formation rate of up to 28-30%, while supplementing the MS medium with a combination of NAA and TDZ resulted in a maximum regeneration of only up to 15%. Based on these observations, the medium used for the regeneration assays was MS medium comprising different concentrations of IBA and TDZ. FIGS. 1A-B shows the effect of growth regulators concentration and two different light conditions on the regeneration of leaf explants obtained from shoot grown in PM medium. Higher regeneration frequency was obtained when leaf explants were cultured for one week in low light intensity (2.5 µmol/m$^2$ s) and subsequently transferred to normal light intensity (40 µmol/m$^2$ s). A combination of 2 mg/l IBA and 2 mg/l TDZ was shown to give the best regeneration frequency of 50.2% with an average of 3.2±0.6 shoots per regenerating explant (FIG. 1A). Sufficient regeneration frequencies (42.6-46.6%) were also obtained when the leaf explants were grown in a medium containing 1 mg/l IBA and 2 mg/l TDZ; however, most of the explants turned brown and formed excessive calli. Culturing of control explants with TDZ only induced significant explants expansion and compact calli formation however with a very low regeneration frequency of ca. 2%. The addition of AC did not positively influenced regeneration. Application of two weeks dark treatment before the exposure of the plants to low light intensity also was not advantage (FIG. 1B).

Hence, cultivating the leaf explants on MS basal medium supplemented with a combination of 2 mg/l IBA and 2 mg/l TDZ, in light conditions of one week low light intensity followed by transfer to normal light was identified as the best conditions for obtaining high regeneration frequencies and increasing the percentage of shoot differentiation.

Figure 2A:
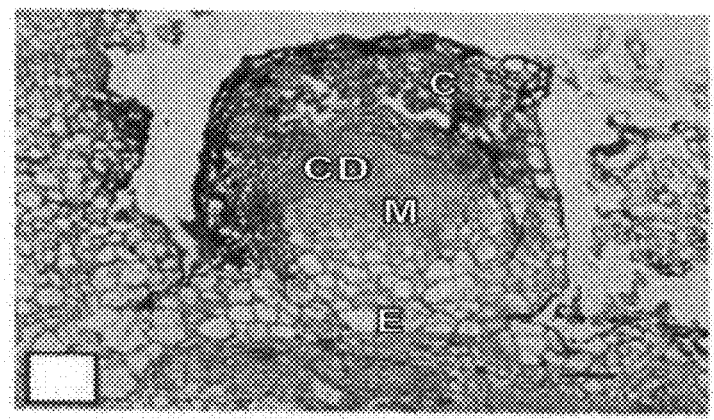
FIGS. 2*a-c* show light microscopy observation of shoot organogenesis in the fig tree. Leaf explants of cv. Brown Turkey were cultivated on medium with IBA (2 mg/l) and TDZ (2 mg/l). (A) After 15 days—the first meristematic domes appeared on the adaxial surface of the explant. Bar=100 μm. (B) After 21 days—adventitious buds and leaf primordia on the adaxial epidermis. Bar=200 μm. (C) After 28 days—adventitious shoots with differentiated apical and axillary meristems and developing leaves. Bar=100 μm; C—callus, CD—cell division, DL—developing leaves, E—epidermis, M—meristem, VS—vascular system.
Figure 2B:
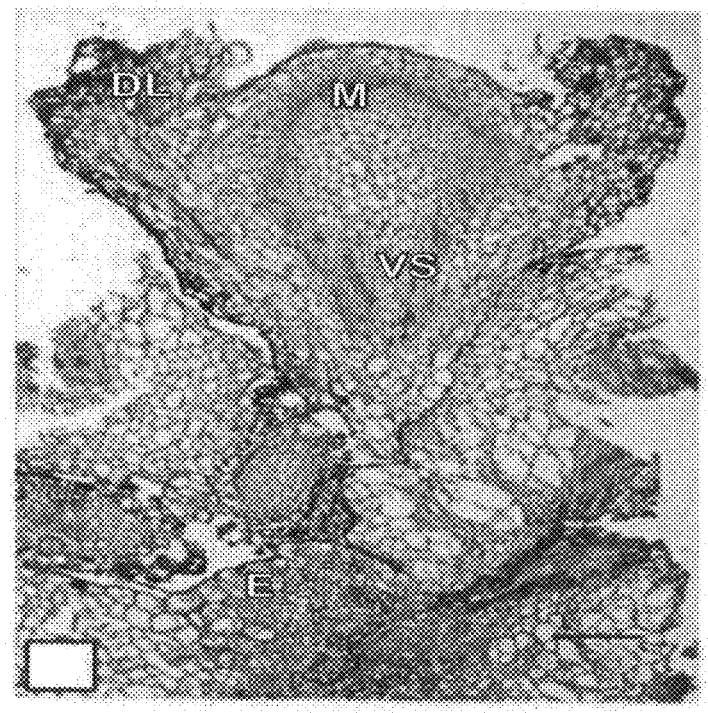
Figure 2C:
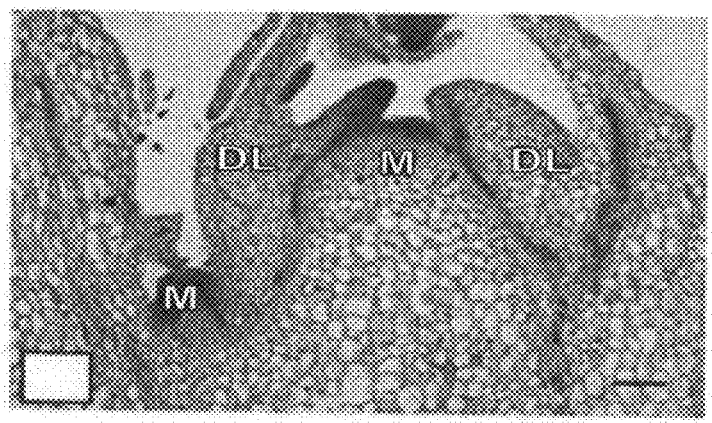

Histological observations (FIG. 2 A-C) showed that the regeneration process followed the developmental pattern of direct organogenesis. Adventitious shoots developed from meristematic centers, appearing in both epidermal and mesophyll tissues. Within 25 days they became visible on the wounded surface of the explant. A prolonged culture up to 42 days resulted in explant expansion, but the developing shoots were surrounded and covered by significant amount of callus, which inhibited their further growth.

Figure 3:
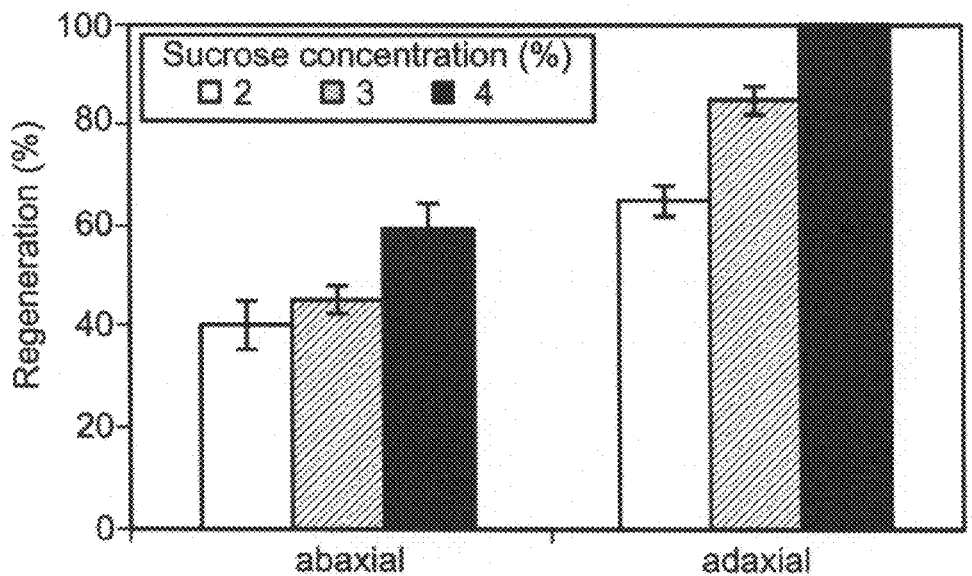
FIG. 3 shows the influence of sucrose concentration and leaf surface position on adventitious shoot regeneration. Leaf explants of cv. Brown Turkey were cultured on medium with TDZ (2 mg $l^{-1}$) and IBA (2 mg $l^{-1}$). Vertical bars indicate standard error (±S.E.).
Figure 4A:
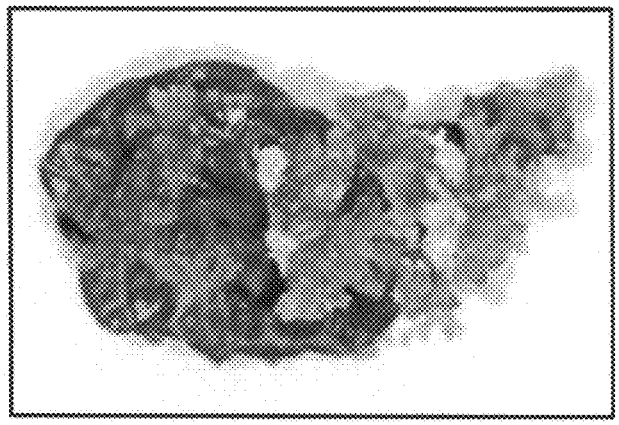
FIGS. 4*a-b* show formation of adventitious shoot in fig cv. Brown Turkey. Stereomicroscopy observation of the leaf explants cultured 4 weeks on regeneration medium (A) with adaxial side up (0.63×0.8) and (B) with abaxial side up (0.63× 1.25).
Figure 4B:
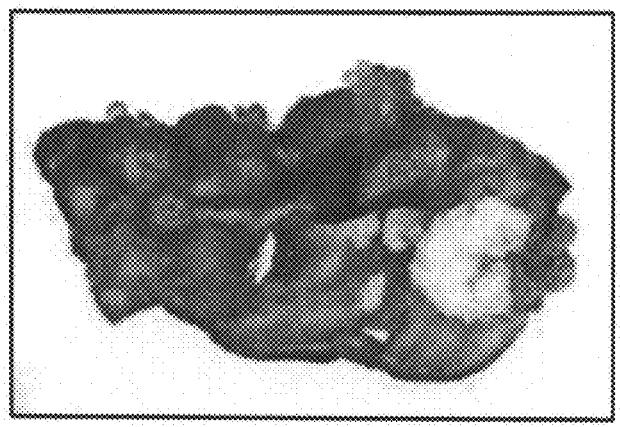

Effect of the Leaf Explants Position on the Solid Medium and the Medium Sucrose Concentration The present invention surprisingly shows that the position of the leaf surface on the medium, in combination with the sucrose concentration in the medium have a significant effect of the leaf explants regeneration. Data presented in FIG. 3 show that cultivating the explants with their adaxial surface up led to a considerable increase in their regeneration frequency. In combination with 4% sucrose, leaf explants cultured with their adaxial side up showed 100% of adventitious shoot formation with more than 5 shoots per regenerating explant. Most of the adventitious shoots developed directly, typically at the wounds sited at the central and distal part of the leaf petiole (FIG. 4A). When the explants were cultured with their abaxial side up, shoot formation occurred on the adaxial side of the leaf only (FIG. 4B), and browning and calli formation were observed.

In conclusion, based on the results described herein above, the optimal conditions for fig regeneration from leaf explants are as follows: leaf explants are isolated from 3-4 weeks old in vitro fig shoot cultures; the explants are placed with their adaxial side up on an MS-based regeneration medium containing 2 mg/l IBA, 2 mg/l TDZ and 4% (w/v) sucrose; explants cultures are exposed to low light intensity (2.5 µmol/m s) for one week and subsequently transferred to normal light (40 µmol/m$^2$ s). Accumulation of the factors that positively influenced regeneration, enable us to develop an efficient and reproducible system for adventitious shoot formation in. This protocol was successfully applied to fig cultivar Brown Turkey and cv. Smyrna and resulted in 100% regeneration with more than 5 shoots per regenerating explant. The regeneration system described herein above was used as a prerequisite for the development of an efficient transformation system.

Rooting Procedure

Figures 5A, 5B, 5C:
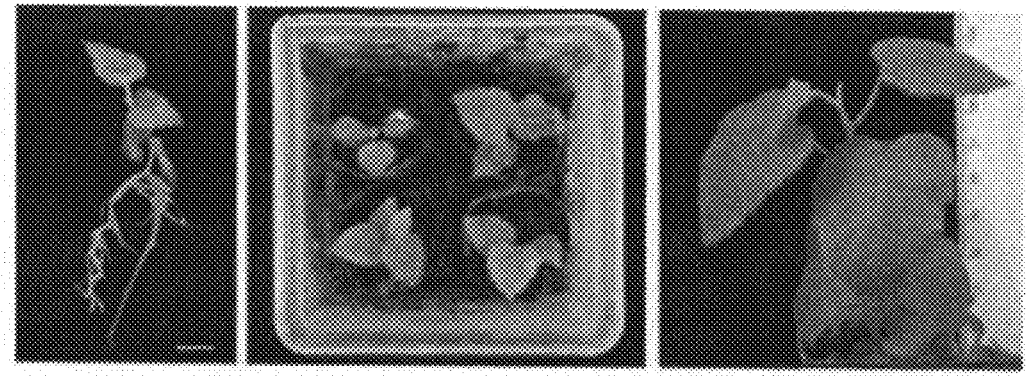
FIGS. 5*a-c* describe rooting and acclimatization of plants from cv. Brown Turkey. (A) In vitro rooted plant (bar 1 cm). (B) Plants in rooting cylinders. (C) Potted plant in the greenhouse one month after acclimatization.

Two methods were examined to obtained root induction (Table 1). According to the first approach, each regenerated shoot was placed in a tube containing root induction medium comprising 2 mg/l IBA. Using this method, ca. 80% of the shoots formed roots. However, insufficient percentage of these plants was successfully acclimatized in the greenhouse conditions. According to the second approach, regenerated shoots were cultured directly in rooting cylinders, with or without 1 mg/l IBA. After 4 weeks showed 100% root formation was achieved, independent on the presence of an auxin. These plants had better hardening and growth characteristics and easier further acclimatization in the greenhouse conditions (FIG. 5).

TABLE 1

Comparison of Methods for Root Formation

| IBA (mg/l) | Root formation (%) ± SE | |
|---|---|---|
| | Rooting in liquid medium | Rooting in solid medium |
| 0 | 8.3 ± 1.59 | 100 |
| 1 | 47 ± 5.43 | 100 |
| 2 | 81.3 ± 7.61 | 83 ± 6.27 |

Example 2

Transformation of *Ficus carica*

Choice of Selective Antibiotic

Figure 6:
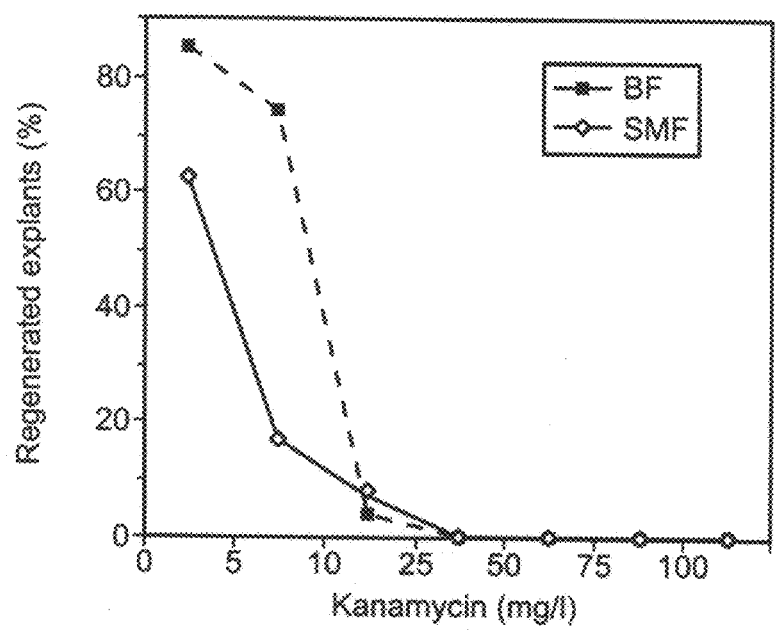
FIG. 6 describes the sensitivity of leaf explants of the fig cvs. Brown Turkey and Smyrna to kanamycin.

In order to use kanamycin as a selection agent for transformed cells, non-inoculated leaf explants from in vitro fig cultures of both cultivars Brown Turkey and Smyrna were tested for their tolerance to kanamycin. Wounded leaves were placed on a regeneration medium supplemented with kanamycin at a concentration selected from 0, 10, 25, 50, 75 and 100 mg/l. The minimal concentration for inhibition of adventitious shoot induction for cv. Brown Turkey was 25 mg/l. However with cv. Smyrna, a few single buds were formed at 25 mg/l kanamycin, but they remained white and did not develop further (FIG. 6 Km sensitivity). Therefore, the concentration of 50 mg/l kanamycin was initially chosen for selection in the subsequent transformation experiments.

Regeneration of Transgenic Shoots

Leaf explants of 3-4 weeks old in vitro propagated *Ficus carica* plants were wounded across the main vein and co-cultivated with the disarmed strain EHA105 harboring the plasmid pME504, comprising the genes GUS-int and npt II. Following co-cultivation with *A. tumefaciens*, explants were initially placed on regeneration medium supplemented with 50 mg/l kanamycin and 150 mg/l ticarcillin and cultured with their adaxial side up. The leaf explants were exposed for one week to low light intensity and then transferred to normal light. Under the selective conditions of 50 mg/l kanamycin, up to 30% of the explants of Brown Turkey and up to 50% of Smyrna formed green shoots after 4 weeks of culture. The regenerating shoots were transferred to PR medium supplemented with 100 mg/l kanamycin and 150 mg/l ticarcillin for further selection. Following this scheme of selection the transformation frequency established for cv. Brown Turkey varied between the experiments from 1.7 to 10% and from 2.1 to 7.8% for cv. Smyrna. Our observations showed that cultivation of the new emerging transgenic shoots more than 3 subcultures in selective conditions of 100 mg/l kanamycin on proliferation medium resulted in inhibition of their growth and development. Therefore, the following design of regeneration/selection process was concluded: one subculture (4 weeks) on regeneration medium with 50 mg/l kanamycin and 150 mg/l ticarcillin followed by two subcultures (6 weeks) of the isolated shoots on PM with 100 mg/l kanamycin and 150 mg/l ticarcillin and finally one subculture only with ticarcillin (150 mg/l). Then leaves from the putative transgenic plants were subjected to GUS staining. GUS positive plants were grown as individual clones on PM with 50 mg/l kanamycin with or without ticarcillin (150 mg/l) and subjected for molecular analysis.

In order to increase the efficiency of the selection a set of additional experiments was performed. Following co-cultivation with *Agrobacterium tumefaciens* on solid medium the explants were cultured for 0, 3, 7 and 10 days in liquid regeneration medium containing 50 mg/l kanamycin and ticarcillin (150 mg/l). Leaves were placed in 10 ml liquid selection medium with addition of 0.5 ml Amberlite XAD-7 (Sigma) in Erlenmeyer (100 ml) in orbital shaker (85 rpm). The liquid selection medium and amberlite were changed every 3 days. Then the explants were blotted dry and transferred to solid selection medium with 100 mg/l kanamycin and ticarcillin (150 mg/l) for the completion of total of four weeks. Following this scheme of selection the transformation frequency established for cv. Brown Turkey varied between the experiments from 6 to 12% for cv. Smyrna it was from 4 to 10% respectively.

Histochemical GUS Assay

Figure 7A:
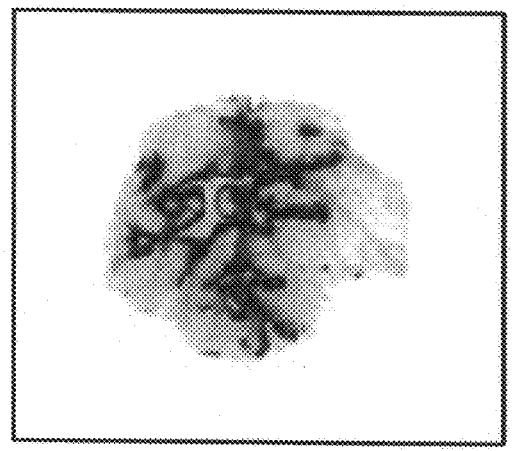
FIGS. 7*a-d* show histochemical GUS analysis by stereomicroscope observations. (A) Transient GUS expression 3 days after inoculation of leaf explants of Brown Turkey (0.63×1.0). (B) GUS staining of regenerating leaf explants after four weeks culture in selection of 50 mg/l kanamycin and 150 mg/l ticarcillin (0.63×2.5). (C) GUS expression detected in the leaves of isolated putatively transformed shoot of cv. Brown Turkey and (D) cv. Smyrna cultured on PM with 100 mg/l kanamycin and 150 mg/l ticarcillin (0.63×2.0).
Figure 7B:
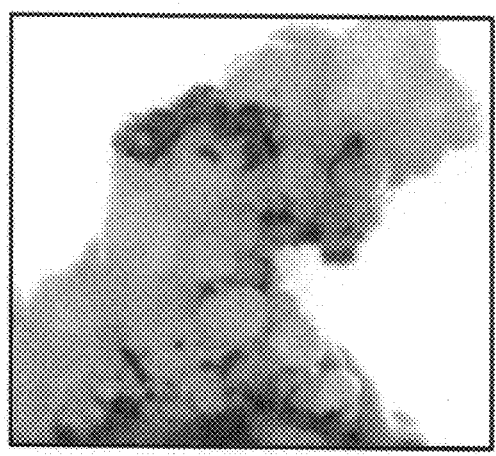
Figure 7C:
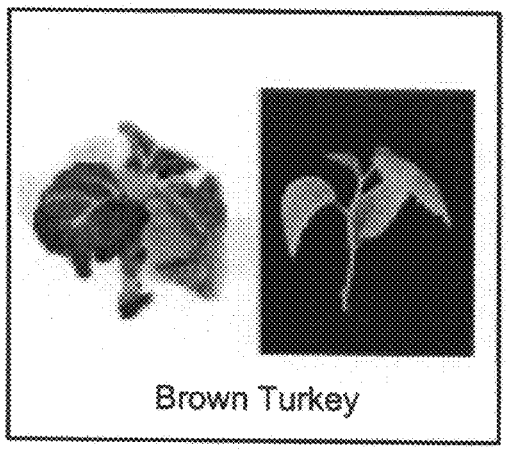
Figure 7D:
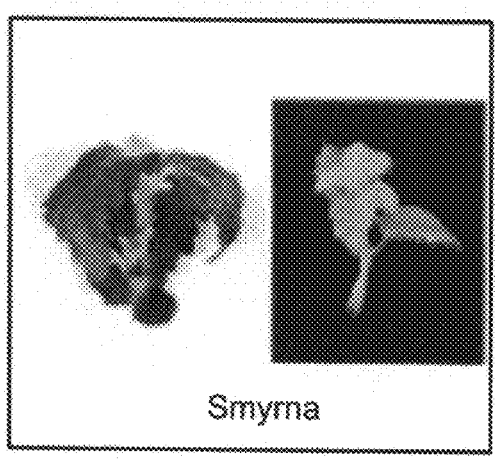
Figure 10:
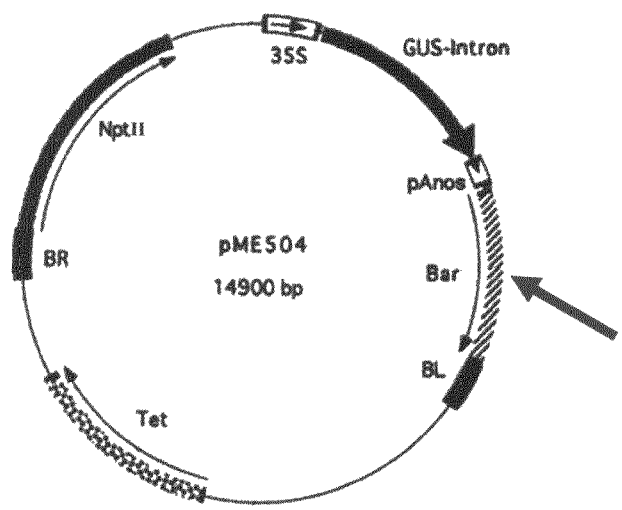
FIG. 10 is a schematic illustration showing a map of the pME504 construct, carrying the nptII, the uidA-intron genes and the bar gene under the control of the CaMV 35S promoter.

Transient GUS expression reveals a high gene transfer rate only for leaves that have been blotted during the co cultivation period with their adaxial side up. Histochemical GUS analysis done 3 and 7 days after infection showed that between 95 and 100% of the explants of both cultivars had large infected sites, when cultured with their adaxial side up. However when cultured with their abaxial side up no transient GUS expression was observed in the two fig varieties examined (FIG. 7 A) After four weeks in selective conditions (kanamycin 50 mg/l) part of the regenerating explants (20 leaves) stained histochemically and positive GUS shoots were counted. Observation under stereomicroscope (FIG. 7 B) of the leaves of cv. Brown Turkey showed that 7.46% (10 out of 134) of the shoots were GUS positive and 92.53% escaped transformation. An in situ β-glucuronidase assay was carried out to further confirm the integration and expression pattern of the transformed marker genes. Intact plants of all the selected shoots propagated on a medium containing kanamycin and control (wild type) plants were tested. GUS expression was observed in the leaves of the transgenic fig plants cv. Brown Turkey (FIG. 7 C) and Smyrna (FIG. 7C).

Molecular Confirmation of Transformation

PCR analysis of the putative transgenic shoots confirmed the stable incorporation of the transgenes into the *Ficus carica* genome. All clones selected after transformation with pME504 showed the predicted bands—the 645 bp for the npt II gene and the 676 bp for the uidA-intron (GUS) (FIG. 8 A-B). No fragment was amplified in the control, untransformed plant (not shown).

Southern blot analysis on HindIII digested genomic DNA from one putative transgenic plants of Brown Turkey and one putative transgenic plants of Smyrna, randomly chosen, provided additional molecular evidence to the incorporation of foreign DNA (FIG. 9). The Southern blot data are consistent with the plasmid (pME504) restriction map. No hybridization bands were present in the control, untransformed plants (not shown). Southern blot analysis on Hind III digested DNA from the putative transgenic plant provided additional evidence for the incorporation of the foreign DNA. The hybridization pattern in Smyrna indicated insertion of the T-DNA into two different loci (FIG. 9).

Example 3

Transgenic 'Brown Turkey' Plants Generated According to the Teachings of the Present Invention Expressing the Bar Herbicide Selective Marker Bialaphos, a non-selective herbicide, is a tripeptide composed of two L-Ala residues and an analog of Glu known as phosphinothricin (PPT). Bialaphos is toxic to bacteria and plants after intracellular peptidases remove the Ala residues and release active PPT, an inhibitor of Gln synthetase (GS). Inhibition of GS by PPT causes a rapid buildup of intracellular ammonia levels. The associated disruption of chloroplast structure results in inhibition of photosynthesis and plant cell death. There is thus a widely recognized need for generating plants resistant to PPT, Basta.

Transgenic 'Brown Turkey' plants expressing the bar gene, were generated using the teachings of the present invention. Such plants are expected to display resistance to the herbicide phosphinothricin (PPT, 'Basta').

Experimental Procedures and Results

Figure 11:
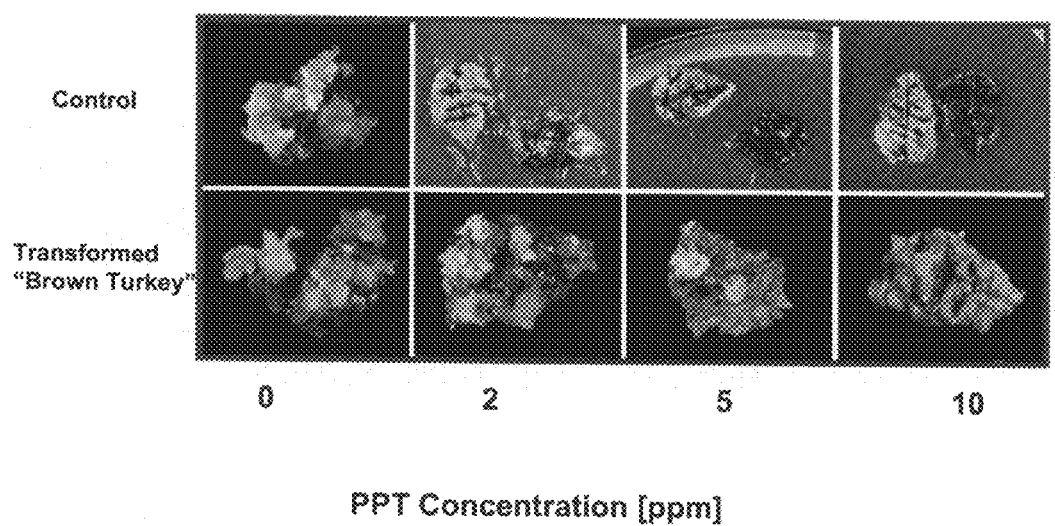
FIG. 11 depict herbicide resistance in control and transgenic Brown Turkey cv treated with increasing concentrations of PPT.

The pME504 plasmid which comprises the bar gene [*Streptomyces hygroscopicus* bar gene conferring resistance to herbicide bialaphos (X05822) Thompson, C. J., Movva, N. R., Tizard, R., Crameri, R., Davies, J. E., Lauwereys, M. and Botterman, J. Characterization of the herbicide-resistance gene bar from *Streptomyces hygroscopicus* EMBO J. 6, 2519-2523 (1987)] was used to transform 'Brown Turkey' plants. Herbicide resistance in control and transgenic Brawn Turkey cv. tissue culture line 001 was evaluated. As shown in FIG. 11, non-transformed plants showed signs of necrosis and chlorosis on basal leaves following two days and died one week later (FIG. 11). Resistant lines, however, were propagated in vitro even on 10 ppm Basta (FIG. 11).

These results demonstrate that the heterologous expression of the bar gene in fig is associated with resistance to the herbicide phosphinothricin.

The possibility of the use of the bar gene as a selectable marker in transgenic experiments was also evaluated.

Figure 12:
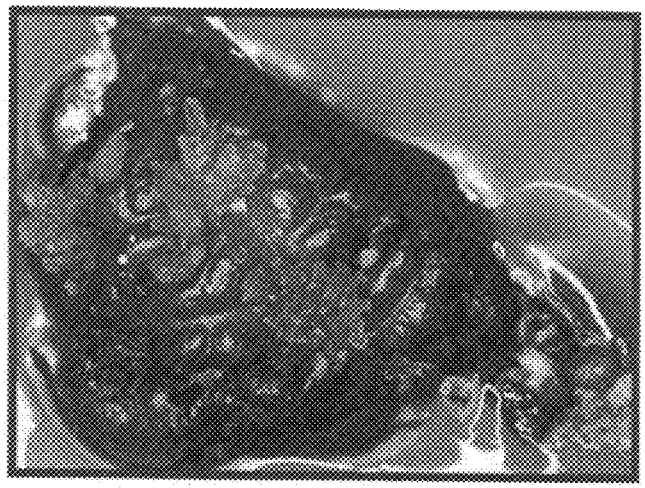
FIG. 12 shows transgenic regeneration of 'Brown Turkey' fig cultivar transformed with pME504 and selection on 5 ppm BASTA.

Transformation of 'Brown Turkey' fig cultivar with pME504, as above, and selection on 5 ppm BASTA yielded seven plants with transformation frequency of 3.5% (FIG. 12).

These result demonstrate the feasibility of using the bar gene as a selectable marker that could replace the antibiotic resistance gene in fig.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. A method for producing transgenic *Ficus* species comprising:
   (a) co-culturing at least one *Ficus* leaf explant abaxial side up on a solid co-culturing medium with *Agrobacterium* harboring a genetic construct which comprises at least one exogenous polynucleotide to form a putatively transformed leaf explant;
   (b) placing said putatively transformed leaf explant, adaxial side up, on a solid culturing medium under conditions which promotes shoot formation;
   (c) selecting a transformed adventitious shoot; and
   (d) culturing the transformed adventitious shoot to form a transgenic *Ficus* plant.

2. The method of claim 1, wherein the leaf explant is obtained from an in vitro *Ficus* culture.

3. The method of claim 1, wherein the leaf explant is wounded before said co-culturing with *Agrobacterium*.

4. The method of claim 1, wherein the *Agrobacterium* is *A. tumefaciens*.

5. The method of claim 1, wherein said solid culturing medium and said solid co-culturing medium comprises at least one auxin and at least one cytokinin.

6. The method of claim 1, wherein said conditions which promote shoot formation comprise culturing under a light intensity in the range of 1-5 µmol/m s for one week; and subsequently culturing under a light intensity in the range of 10-60 µmol/m² s.

7. The method of claim 1, wherein said solid culturing medium comprises at least one auxin, at least one cytokinin and at least one carbon source.

8. The method of claim 7, wherein said solid culturing medium further comprises at least one selection agent.

9. The method of claim 8, wherein said at least one selection agent is an antibiotic.

10. The method of claim 1, wherein the genetic construct further comprises a selection marker.

11. The method of claim 10, wherein the selection marker is a gene inducing antibiotic resistance or a gene inducing herbicide resistance.

12. The method of claim 9, wherein said at least one selection agent comprises kanamycin and ticarcillin.

13. The method of claim 1 wherein a frequency of shoot formation per transformed leaf explant is at least five shoots.

14. The method of claim 1, wherein the genetic construct further comprises at least one regulatory element.

15. The method of claim 14, wherein the regulatory element is selected from the group consisting of a promoter, an enhancer, a terminator, a transposable element and a post-transcriptional element.

16. The method of claim 1, wherein the exogenous polynucleotide is homologous to the *Ficus* genome.

17. The method of claim 16, wherein the exogenous polynucleotide is selected from the group consisting of a polynucleotide encoding a polypeptide and an antisense polynucleotide.

18. The method of claim 16, wherein the exogenous polynucleotide confers a desirable agronomical trait selected from the group consisting of insect tolerance, disease resistance, herbicide tolerance, cold tolerance, drought tolerance and salinity tolerance.

19. The method of claim 1, wherein the exogenous polynucleotide is heterologous to the *Ficus* genome.

20. The method of claim 19, wherein the exogenous polynucleotide encodes a foreign protein.

21. The method of claim 20, wherein the foreign protein is expressed in the latex serum produced by the plant.

22. The method of claim 20, wherein the foreign protein is expressed in a fruit of the plant.

23. The method of claim 20, wherein the foreign protein is selected from the group consisting of an anti-cancer agent, an antioxidant and a protein eliciting an immunogenic response in a mammal.

24. The method of claim 23, wherein the foreign protein is a protein eliciting an immunogenic response in a mammal.

25. The method of claim 1, wherein the transgenic *Ficus* is *Ficus carica*.

26. The method of claim 5, wherein said at least one cytokinin comprises thidiazuron (N-phenyl-N'-(1,2,3-thiadiazol-5-yl)urea, TDZ) and said at least one auxin comprises indole-3-butyric acid (IBA) or 2,4-dichlorophenoxy acetic acid (2,4-D).

* * * * *